(12) United States Patent
Yamashita

(10) Patent No.: US 10,570,067 B2
(45) Date of Patent: Feb. 25, 2020

(54) COMPOSITIONS FOR ENHANCING POLLINATION AND METHODS FOR USING SAME

(71) Applicant: Thomas T. Yamashita, Turlock, CA (US)

(72) Inventor: Thomas T. Yamashita, Turlock, CA (US)

(*) Notice: Subject to any disclaimer, the term of this patent is extended or adjusted under 35 U.S.C. 154(b) by 20 days.

(21) Appl. No.: 15/836,495

(22) Filed: Dec. 8, 2017

(65) Prior Publication Data

US 2018/0099911 A1 Apr. 12, 2018

Related U.S. Application Data

(62) Division of application No. 14/198,360, filed on Mar. 5, 2014, now Pat. No. 9,868,676.

(60) Provisional application No. 61/783,916, filed on Mar. 14, 2013.

(51) Int. Cl.

| | |
|---|---|
| *C05G 3/00* | (2006.01) |
| *C05D 9/02* | (2006.01) |
| *C05F 11/02* | (2006.01) |
| *A23K 20/163* | (2016.01) |
| *A23K 20/10* | (2016.01) |
| *A23K 20/20* | (2016.01) |
| *A23K 50/90* | (2016.01) |
| *A01N 25/12* | (2006.01) |

(52) U.S. Cl.
CPC .............. *C05G 3/00* (2013.01); *A01N 25/12* (2013.01); *A23K 20/10* (2016.05); *A23K 20/163* (2016.05); *A23K 20/20* (2016.05); *A23K 20/30* (2016.05); *A23K 50/90* (2016.05); *C05D 9/02* (2013.01); *C05F 11/02* (2013.01)

(58) Field of Classification Search
CPC ..................................................... A23K 50/90
See application file for complete search history.

(56) References Cited

U.S. PATENT DOCUMENTS

| | | | |
|---|---|---|---|
| 4,229,442 A | 10/1980 | Pinckard | |
| 5,165,245 A | 11/1992 | Agrawal et al. | |
| 5,549,729 A | 8/1996 | Yamashita | |
| 5,582,627 A | 12/1996 | Yamashita | |
| 5,696,094 A | 12/1997 | Yamashita | |
| 5,797,976 A | 8/1998 | Yamashita | |
| 6,187,326 B1 | 2/2001 | Yamashita | |
| 6,241,795 B1 | 6/2001 | Svec et al. | |
| 6,309,440 B1 | 10/2001 | Yamashita | |
| 6,318,023 B1 * | 11/2001 | Yamashita | A01G 7/06 47/57.6 |
| 6,336,772 B1 | 1/2002 | Yamashita | |
| 6,383,245 B1 | 5/2002 | Yamashita | |
| 6,475,258 B1 | 11/2002 | Yamashita | |
| 6,524,600 B2 | 2/2003 | Yamashita | |
| 6,871,446 B1 | 3/2005 | Yamashita | |
| 6,874,277 B2 | 4/2005 | Yamashita | |
| 6,953,585 B2 | 10/2005 | Yamashita | |
| 7,261,902 B2 | 8/2007 | Yamashita | |
| 7,501,006 B2 | 3/2009 | Rogers et al. | |
| 2005/0158355 A1 | 7/2005 | Yamashita | |
| 2005/0197252 A1 | 9/2005 | Yamashita | |
| 2006/0083725 A1 | 4/2006 | Dean | |
| 2011/0005960 A1 | 1/2011 | Guha et al. | |

FOREIGN PATENT DOCUMENTS

| | | |
|---|---|---|
| DE | 1932225 B1 | 12/1970 |
| WO | WO95022900 A1 | 8/1995 |
| WO | WO2009042811 A1 | 4/2009 |

OTHER PUBLICATIONS

Olive flowering and pollination—2018 (Year: 2018).*
Humates 2009 (Year: 2009).*
Confectioner-s Sugar Composition—2008 (Year: 2008).*
Confectioner's sugar, chemical structure, molecular formula, reference standards, 2008, 1 page.
Humates: Nomenclature, Sources and Quality, 2009, 5 pages.
Morgano et al., A Comprehensive Investigation of the Mineral Composition of Brazilian Bee Pollen:Geographic and Seasonal Variations and Contribution to Human Diet, J. Braz Chem Soc (2012), 23(4):727-736.

* cited by examiner

*Primary Examiner* — John Pak
(74) *Attorney, Agent, or Firm* — Khin K. Chin; Bret E. Field; Bozicevic, Field & Francis LLP

(57) ABSTRACT

Aspects of the invention include compositions for enhancing pollination. Dry compositions according to certain embodiments include a carbon skeleton energy compound, macronutrients, a vitamin cofactor composition, micronutrients, an ionophore, and a source of extracted humate. Methods for using the dry compositions of the invention to enhance pollination are also described.

18 Claims, 4 Drawing Sheets

COMPOSITIONS FOR ENHANCING POLLINATION AND METHODS FOR USING SAME

CROSS-REFERENCE TO RELATED APPLICATIONS

This application is a divisional of U.S. patent application Ser. No. 14/198,360 filed Mar. 5, 2014, which application claims priority to the filing date of to U.S. Provisional Patent Application Ser. No. 61/783,916, filed Mar. 14, 2013; the disclosure of which applications is incorporated herein by reference.

INTRODUCTION

Effective pollination of many agronomic species is not a simple event. In many cases the period of flowering coincides with non-ideal environmental conditions such as cold and wetness. There are natural deterrents of effective pollination, including apparent varietal incompatibility, variations in plants that render them capable or incapable of securing effective pollination. Likewise, the ability of the honeybee to pollinate may be diminished due to poor nutrition or attractants to the flora to be pollinated, further limiting the effective pollination of targeted flora.

Pollination enhancers and honeybee attractants may be employed to increase effective pollination by introducing a pollination enhancer into a plant's environment, such as through application onto plant foliage. There is a continued need to develop compositions which enhance pollination and improve honeybee nutrition to improve effective pollination of targeted flora.

SUMMARY

Aspects of the invention include compositions for enhancing pollination. Dry compositions according to certain embodiments include a carbon skeleton energy compound, macronutrients, a vitamin cofactor composition, micronutrients, an ionophore, and a source of extracted humate. Methods for using the dry compositions of the invention to enhance pollination are also described.

In embodiments of the invention, dry compositions for enhancing pollination are provided and include a carbon skeleton energy compound, macronutrients, a vitamin cofactor composition, micronutrients, an ionophore, and a source of extracted humate. In some embodiments, the source of extracted humate includes leonardite fines. In these embodiments, the leondardite fines is a complexing agent as well as a source of exotic micronutrients. In some embodiments, compositions of interest further include pollen. In certain instances, pollen includes pure pollen grains obtained from the target flora for enhanced pollination. In embodiments of the invention, compositions are dry and are applied as a powder to target flora or a source of biotic vectors.

Aspects of the invention also include methods for using the subject dry compositions to enhance pollination in one or more plants. In some instances, methods include administering the composition to plant foliage by a hand-held applicator. In other instances, methods include administering the composition to plant foliage by aircraft (e.g., helicopter, airplane). In certain embodiments, methods include applying the dry composition to a source of biotic vectors (e.g., beehive) while in conjunction with applying the dry composition to the foliage of one or more plants. In yet other embodiments, methods include applying the dry composition to a source of biotic vectors as a nutritional supplement and activator of biotic vector activity prior to applications for enhanced pollination.

Applications for the subject composition include increasing the effective cross-pollination of subject flora, such as by: increasing the number of biotic vectors which visit the site of target flora (e.g., fruit orchards); increasing the amount of time a biotic vector will spend at the site of target flora; increasing the specificity of biotic vectors for a particular target flora; improving the overall nutritional health and activity of biotic vectors as well as increasing the overall production of crops from enhanced pollination; and the like.

DETAILED DESCRIPTION

Figure 1:
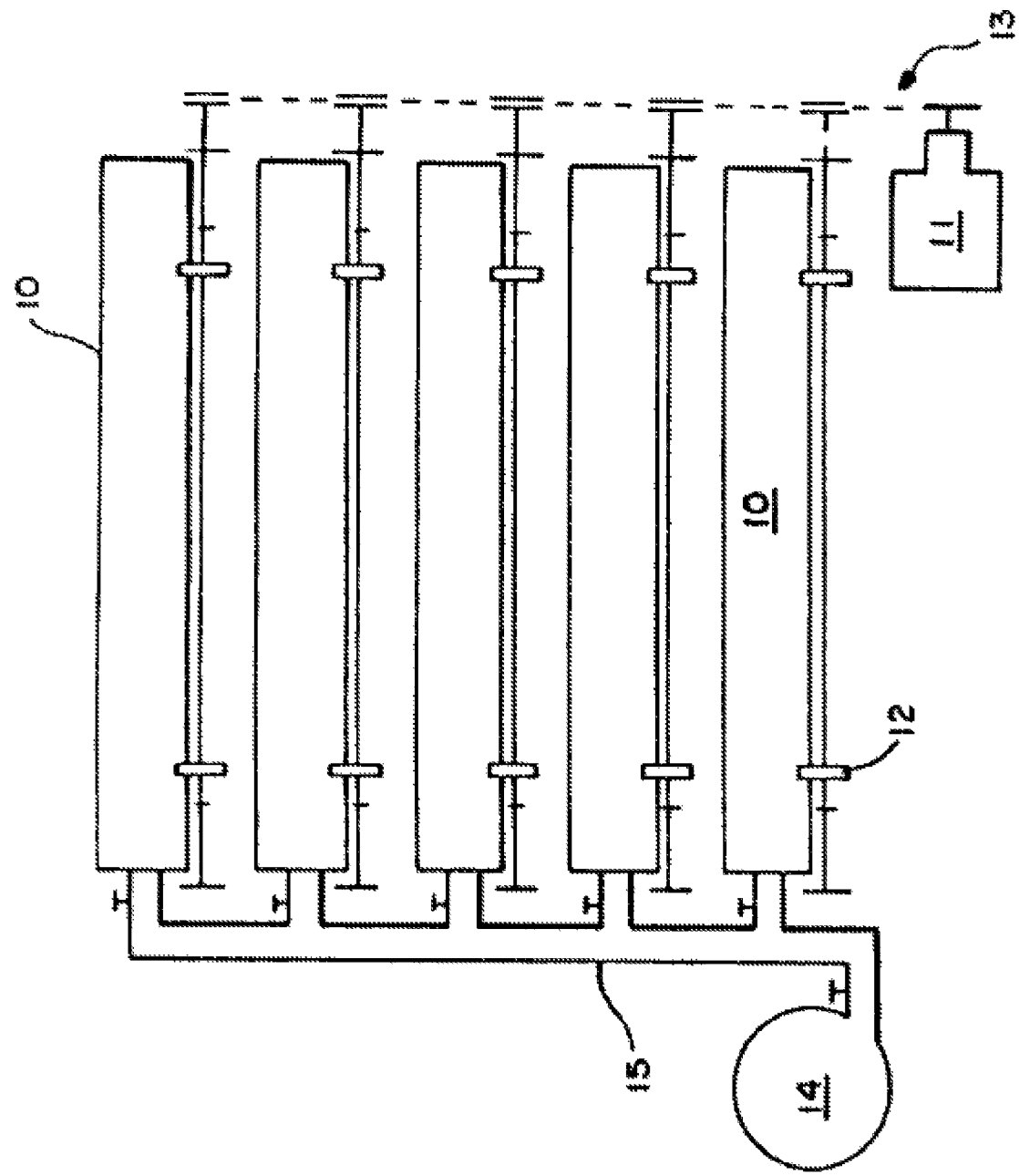
FIG. 1 is a diagrammatic top view of drying apparatus for processing pollen according to certain embodiments.

Aspects of the invention include compositions for enhancing pollination. Dry compositions according to certain embodiments include a carbon skeleton energy compound, macronutrients, a vitamin cofactor composition, micronutrients, an ionophore, and a source of extracted humate. Methods for using the dry compositions of the invention to enhance pollination are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present invention provides dry compositions having a source of extracted humate for enhancing pollination. In further describing embodiments of the invention, compositions having a carbon skeleton energy compound, macronutrients, a vitamin cofactor composition, micronutrients, an ionophore, and a source of extracted humate are first reviewed in greater detail. Next, methods for using the subject compositions for enhancing pollination are described. Kits including one or more of the subject dry compositions are also described.

Dry Compositions for Enhancing Pollination

As summarized above, the subject invention provides dry compositions for enhancing pollination. The term "enhancing pollination" is used in its conventional sense to refer to increasing overall effective cross pollination by biotic vectors such that a greater number of subject flora are pollinated when compositions of interest are applied as compared to flora not applied the subject compositions. The term "biotic vectors" is used herein in its conventional sense to refer to pollen carrying organisms which move pollen from the male anthers to the female stigma of a flower to accomplish syngamy of the female gamete in the ovule of a flower by the male gamete in the pollen. Biotic vectors may include, but are not limited to insects such as bees, honeybees, bumblebees, orchard mason bees, leaf cutter bees, bluebottle flies, wasps, bee flies, butterflies, moths, beetles, flies, midges, thrips, fruit flies, horse flies and vertebrates, such as bats, hummingbirds, honeyeaters, sunbirds, among other types of pollinators. In certain embodiments, biotic vectors are honeybees.

As described in greater detail below, the subject compositions may enhance pollination by increasing the number of biotic vectors which visit the subject flora, improving the specificity of biotic vectors for the subject flora, improving the overall nutritional health and activity of biotic vectors or increasing the amount of time biotic vectors spend at the subject flora to increase effective cross pollination. For example, in some instances compositions provided herein may increase effective cross pollination by 5% or more, such as by 10% or more, such as by 25% or more, such as by 50% or more, such as by 75% or more, such as by 90% or more, such as by 95% or more and including by 100% or more as compared to flora not applied the subject compositions. In other instances, compositions of interest may increase effective cross pollination by 1.5-fold or greater, such as 2-fold or greater, such as 2.5-fold or greater, such as 3-fold or greater, such as 5-fold or greater and including increasing effective cross pollination by 10-fold or greater.

Alternatively, in certain embodiments enhanced pollination may be realized by a particular goal, where in some instances the desired enhancement is an increase in cross pollination that ultimately results in greater production of some desirable parameter, such as for example the amount of harvested crop produced by the subject flora. For example, enhanced pollination by compositions of interest may be realized by increased amount of harvested crop by 10% or more, such as 25% or more, such as 50% or more, such as 75% or more and including increasing the amount of harvested crop by 100% or more. In other instances, compositions of interest may increase harvested crop production by 1.5-fold or greater, such as 2-fold or greater, such as 2.5-fold or greater, such as 3-fold or greater, such as 5-fold or greater and including increasing effective cross pollination by 10-fold or greater. For instance, where the harvested crop are fruits or nuts, compositions and methods for enhancing pollination provided by the invention may increase the amount of crop produced by 250 pounds per acre or more, such as 500 pounds per acre or more, such as 1000 pounds per acre or more, such as 1500 pounds per acre or more and including by 2000 pounds per acre or more.

In embodiments of the invention, compositions for enhancing pollination are dry. By "dry" is meant that the subject compositions contain little to no water. Accordingly, compositions of interest are formulations which include 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. As such, compositions of the invention are solid compositions provided in fine grain or powder form. Depending on the desired action of the pollination enhancing compositions and type of subject flora, the size of particles of the compositions varies ranging from 0.01 μm to 100 μm, such as from 0.1 μm to 75 μm, such as from 1 μm to 50 μm, such as from 2.5 μm to 25 μm and including from 5 μm to 10 μm. In certain embodiments, compositions include particles which all have the same size (i.e., are monodisperse or uniform). In other embodiments, compositions include particles which have varying sizes (i.e., are poydisperse). For example, where the subject composition has uniform particle sizes, each component of the composition may be passed through a mesh screen (e.g., a 2-mesh screen) sufficient to uniformly reduce the granular size of each component. In other embodiments, each component may have distinct particle sizes resulting in a polydisperse powder composition.

In certain embodiments, compositions of interest are hygroscopic powders and precautionary measures need be taken to prevent absorption of atmospheric moisture, such as for example by including a dessicant, as described in greater detail below.

As summarized above, compositions of interest are dry compositions for enhancing pollination and include a carbon skeleton energy compound (CSE), macronutrients, a vitamin cofactor composition, micronutrients, an ionophore, and one or more sources of extracted humate. Each of the different components of the compositions is now reviewed in greater detail. The amount of each component may vary in the subject compositions depending on the amount and type of subject flora or method employed. As such, the amounts of each component may be varied as desired, such as by increasing or reducing the amount or ratio of a particular component in the composition prior to application.

One or More Sources of Extracted Humate

In embodiments of the invention, dry compositions include one or more sources of extracted humate. The term "source of extracted humate" as used herein refers to naturally occurring deposits of humate, including oxidized coal, oxidized bituminous material, ironite, volcanic rock, shale, fossilized peat, moss, kelp or seaweed and the like. As such, the subject compositions include, in certain embodiments, powder or fine forms of oxidized coal, oxidized bituminous material, ironite, volcanic rock, shale, fossilized peat, moss, kelp or seaweed and the like. Sources of extracted humate that find use in the subject compositions include organic and inorganic containing substances which, in certain instances, provide a source of a complexing agent and one or more exotic micronutrients.

In certain embodiments, the source of extracted humate in compositions of interest is oxidized coal, such as for example leonardite fines. Leonardite fines, as described herein, refer to the powder form of the vitreous mineraloid oxidation product of lignite or derivative from the sediments enriched in humic acids leached from topsoil or overlain lignite. Depending on the source, leonardite fines included in compositions of interest may vary such that the leonardite fines:

have a humic acid content ranging from 30% w/w to 90% w/w humic acid, such as 65% w/w to 85% w/w humic acid such as 70% w/w to 80% w/w humic acid and including 75% w/w humic acid;

have a fulvic acid content ranging from 5% w/w to 15% w/w fulvic acid, such as 6% w/w to 14% w/w fulvic acid, such as 7% w/w to 12% w/w fulvic acid and including 8% w/w fulvic acid; and have one or more ionic species in an amount which ranges from 0.01 part per billion to 0.1 part per million w/w, where the ionic species include Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium (Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silica (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

For example, in some embodiments compositions of the invention include leonardite fines having a humic acid content ranging from 50% w/w to 80% w/w, a fulvic acid content ranging from 5% w/w to 10% w/w and include at least 5 or more ionic species in a range from 0.01 part per billion w/w to 0.1 part per million w/w. In other embodiments, compositions include leondardite fines having a humic acid content ranging from 50% w/w to 80% w/w and a fulvic acid content ranging from 5% w/w to 10% w/w and include at least 10 or more ionic species in a range from 0.01 part per billion w/w to 0.1 part per million w/w.

The amount of the source of extracted humate in compositions of the invention may vary. For example, the amount may range from 0.01 to 100 pounds, such as from 0.025 to 80 pounds, such as from 0.05 to 70 pounds, such as from 0.1 to 50 pounds and including from 0.1 to 40 pounds. As such, the weight percent of the source of extracted humate in the subject compositions may range from 0.01% to 3% w/w, such as 0.05% to 2% w/w, such as 0.1% to 1.5% w/w and including 0.1% to 1% w/w. Where the source of extracted humate in compositions of interest are leonardite fines, the amount may range from 0.01 to 50 pounds, such as from 0.025 to 40 pounds, such as from 0.05 to 37.5 pounds, such as from 0.1 to 25 pounds and including from 0.1 to 20 pounds. As such, the weight percent of leonardite fines in the subject compositions may range from 0.01% to 3% w/w, such as 0.05% to 2% w/w, such as 0.1% to 1.5% w/w and including 0.1% to 1% w/w.

In certain embodiments, compositions of the invention include two or more sources of extracted humate, such as where the subject compositions include three or more sources of extracted humate, such as 4 or more sources of extracted humate and including 5 or more sources of extracted humate. For example, certain compositions include leonardite fines and fulvic acid fines.

The term "fulvic acid" is used in its conventional sense to refer to the low molecular weight and high oxygen containing humic acids formed primarily by the degradation of plant matter, such as lignin. Where the subject compositions include fulvic acid fines either alone or in combination with one or more other sources of extracted humate, the amount of fulvic acid in compositions of interest may range from from 0.01 to 50 pounds, such as from 0.025 to 40 pounds, such as from 0.05 to 37.5 pounds, such as from 0.1 to 25 pounds and including from 0.1 to 20 pounds. As such, the weight percent of fulvic acid fines in the subject compositions may range from 0.01% to 3% w/w, such as 0.05% to 2% w/w, such as 0.1% to 1.5% w/w and including 0.1% to 1% w/w.

Where compositions include a combination of leonardite fines and fulvic acid fines, the mass ratio of leonardite fines and fulvic acid fines may vary, ranging between 1:1 and 1:10, such as 1:2, such as 1:3, such as 1:4, such as 1:5 and including 1:10. In other instances, the mass ratio of fulvic acid fines and leonardite fines ranges between 1:1 and 1:10, such as 1:2, such as 1:3, such as 1:4, such as 1:5 and including 1:10.

Carbon Skeleton Energy Compounds

CSE compounds that find use in the subject compositions are carbon containing substances which provide a readily assimilable source of both carbon and energy. In certain embodiments, the CSE component provides a complex array of various carbon compounds. The carbon skeleton energy component is a $C_2$ to $C_{10}$ containing compound or polymer thereof, e.g., a polymer in which the monomeric units are $C_2$ to $C_{10}$ compounds, such as a polysaccharide, including a $C_4$ to $C_8$ containing compound or polymer.

CSE compounds of interest include: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

In embodiments of the invention, the amount of CSE component in the composition ranges from about 5% to 75% w/w, such as 10% to 60% w/w, such as 15% to 50% w/w, such as 20% to 40% w/w and including 25% to 35% w/w.

The CSE component may be a single carbon containing compound or a combination of two or more different carbon containing compounds. For example, in some embodiments compositions include two or more carbon containing compounds or polymers, such as where the subject compositions include three or more carbon containing compounds or polymers, such as 4 or more carbon containing compounds or polymers and including 5 or more carbon containing compounds or polymers. Where the CSE component includes two more carbon containing compounds or polymers, the percent by weight of each carbon containing compound in compositions of interest may vary, ranging from 5% to 75% w/w, such as 10% to 60% w/w, such as 15% to 50% w/w, such as 20% to 40% w/w and including 25% to 35% w/w. In certain embodiments, the CSE component is a single carbon containing compound or polymer. In some instances, the carbon skeleton energy compound is powdered sugar.

Macronutrients

As noted above, the compositions include one or more macronutrients. As the macronutrient component is a compound that is used by the subject flora, it is typically water soluble so as to be in a form that may be easily used by a plant. The subject compositions may include one or a plurality of macronutrient components. Accordingly, the number of macronutrient components present in a composition may range from 1 to 15 or more, e.g., from 1 to 6, e.g., from 2 to 6.

The total amount of macronutrient component present in a given composition (whether one or a plurality of macronutrients) depends on a variety of factors such as the particular plant to which the composition is to be administered, the particular macronutrient component(s) employed, and the like. In many embodiments, the total amount of macronutrient component in the composition may range from about 0.01% to about 25% w/w, e.g., from about 1% to about 20% w/w, e.g., from about 1 to about 15% w/w. Exemplary macronutrient components include, but are not limited to one or more of: N, P, K, Ca, Mg, S, Cl, Na, C, H, O. For example, certain embodiments may include one or more of the following exemplary macronutrient components:

R—ammonium nitrate, monoammonium phosphate, ammonium phosphate sulfate, ammonium sulfates, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids P—superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium gluconate, calcium glycerophosphate, calcium lactate, calcium oxide, calcium pantothenate, calcium proprionate, calcium saccharate, calcium sulfate, calcium tartrate Mg—magnesium oxide, dolomite, magnesium acetate, magnesium bensoate, magnesium bisulfate, magnesium borate, magnesium chloride, magnesium citrate, magnesium gluconate, magnesium nitrate, magnesium phosphate, magnesium salicylate, magnesium sulfate S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Where the macronutrient component includes two or more compounds, the percent by weight of each macronutrient compound in compositions of interest may vary, ranging from about 0.01% to about 25% w/w, e.g., from about 1% to about 20% w/w, e.g., from about 1 to about 15% w/w. In certain embodiments, the macronutrient component includes a single macronutrient. In certain instances, the macronutrient is calcium gluconate.

Micronutrients

In certain embodiments, the subject compositions may also include one or more micronutrient components. As the micronutrient components are components that are used by a plant, they are typically water soluble components so as to be in a form that may be easily used by a plant. The subject compositions may include one or a plurality of micronutrient components. Accordingly, the number of micronutrient components present in a composition may range from about 1 to about 60 or more, e.g., from about 3 to about 55, e.g., from about 4 to about 50.

The total amount of micronutrient component present in a given composition, whether a single or a plurality of micronutrients depends on the type of subject flora and may range from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w. Micronutrient compounds of interest include, but are not limited to:

Zn—zinc oxide, zinc acetate, zinc benzoate, zinc chloride, zinc citrate, zinc nitrate, zinc salicylate, ziram.

Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate.

Mn—manganese acetate, manganese chloride, manganese nitrate, manganese phosphate.

Cu—cupric acetate, cupric butyrate, cupric chlorate, cupric chloride, cupric citrate, cupric gluconate, cupric glycinate, cupric nitrate, cupric salicylate, cuprous acetate, cuprous chloride.

B—calcium borate, potassium borohydride, borax, boron trioxide, potassium borotartrate, potassium tetraborate, sodium borate, sodium borohydride, sodium tetraborate.

Mo—molybdic acid, calcium molybdate, potassium molybdate, sodium molybdate.

Co—cobaltic acetate, cobaltous acetate, cobaltous chloride, cobaltous oxalate, cobaltous potassium sulfate, cobaltous sulfate.

Where the micronutrient component includes two or more compounds, the percent by weight of each micronutrient compound in compositions of interest may vary, ranging from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w.

Vitamins and Cofactor Composition

Compositions of interest also include one or more vitamin and cofactor compositions. The subject composition may include one or a plurality of vitamin and cofactor components. Accordingly, the number of vitamin and cofactor components present in a composition may range from about 1 to about 20 or more, e.g., from about 3 to about 15, e.g., from about 5 to about 12.

The total amount of vitamin and cofactor component present in a given composition, whether one or a plurality of vitamin/cofactor components depends on a variety of factors such as the subject flora, the particular vitamin cofactor component(s) employed, and the like. In many embodiments, the total amount of vitamin/cofactor component in the composition may range from about 0.001 to 10%, such as 0.01 to 5%, including 0.25 to 3.0% w/w. Vitamin and cofactors of interest include, but are not limited to:

Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract.

Riboflavin—riboflavin acetyl phosphate, flavin adenine dinucleotide, flavin adenine mononucleotide, riboflavin phosphate, yeast, yeast extract.

Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile.

Pyridoxine—pyridoxal phosphate, yeast, yeast extract.

Folic acid—yeast, yeast extract, folinic acid.

Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine.

Pantothenic acid—yeast, yeast extract, coenzyme A.

Cyanocobalamin—yeast, yeast extract.

Phosphatidylcholine—soybean oil, eggs, bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh, B-acetyl-g-O-hexadecyl, L-a-PTCh, B-acetyl-g-O-(octadec-9-cis-e-nyl), L-a-PTCh, B-arachidonoyl, g-stearoyl, L-a-PTCh, diarachidoyl, L-a-PTCh, dibehenoyl(dibutyroyl), dicaproyl, dicapryloyl, didecanoyl, dielaidoyl, 12 diheptadecanoyl, diheptanoyl), DL-a-PTCh dilauroyl, La-PTCh dimyristoyl(dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl)DL-a-PTCh di-O-hexadecyl(dioleoyl, dipalmitoyl, B—O-methyl-g-O-hexadecyl, B-oleoyl-g-O-hexadecyl, B-palmitoyl-g-O-hexadecyl), D-a-PTCh dipalmitoyl, L-a-PTCh, B—O-methyl-g-O-octadecyl, L-a-PTCh, B—(NBD-aminohexanoyl)-g-palmitoyl, L-a-PTCh, B-oleoyl-g-O-palmitoyl(stearoyl), L-a-PTCh, B-palmitoyl-g-oleoyl, L-a-PTCh, B-palmitoyl-a-(pyren 1-yl)hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl.

Inositol—inositol monophosphate, inositol macinate, myo-inositol, epi-inositol, myo-inositol 2,2'anhydro-2-c-hydroxymethyl(2-c-methylene-my-oinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-Myo-inositol triphosphate, scyllo-inositol.

PABA—m-aminobenzoic acid, O-aminobenzoic acid, p-aminobenzoic acid butyl ester, PABA ethyl ester, 3-ABA ethyl ester.

Where the vitamin and cofactor compositions includes two or more compounds, the percent by weight of each vitamin or cofactor compound in compositions of interest may vary, ranging from about 0.001 to 10%, such as 0.01 to 5%, including 0.25 to 3.0% w/w.

Complexing Agents

As noted above, compositions include one or more sources of extracted humate. In embodiments of the invention, the one or more sources of extracted humate serves as a combined complexing agent and source of exotic micronutrient. A "complexing agent" as described herein is an agent that aids in the solubilization of components of the composition and may also serve to tie up ions (e.g., iron or other ions) and preventing formation of precipitates upon application. A complexing agent may be an agent that is capable of complexing with a metal ion. As such, powder or fine forms of oxidized coal, oxidized bituminous material, ironite, volcanic rock, shale, fossilized peat, moss, kelp or seaweed find use in the subject compositions to provide a source of one or more complexing agents.

In some embodiments, composition may further include a secondary complexing agent in addition to the one or more sources of extract humate. If present, the subject composition may include one or a plurality of secondary complexing agents ranging from about 1 to about 35 or more, e.g., from about 1 to about 20, e.g., from about 1 to about 10.

For example, secondary complexing agents of interest may be citric acid, humic acids, lignosulfonate, etc. Other complexing agents of interest include, but are not limited to: citric acid, lignosulfonates, e.g., Ca—, K—, Na—, and ammonium lignosulfonates, amino acids, propionic acid and nucleic acids. In some instances, the secondary complexing agent may be a chelating agent, such as ethylenediamin tetraacetic acid (EDTA), diethylene triamine pentacetic acid (DTPA), nitrolotriacetic acid (NTA), ethylenediaminediacetate (EDDA), ethylenediamindi(o-hydroxyphenylacetic) acid (EDDHA), hydroxyethylethylene-diaminetriacetic acid (HEDTA), cyclohexane diamine tetraacetic acid (CDTA) and the like. Naturally occurring chelating agents may also be employed. By naturally occurring chelating agent is meant that the chelating agent is a chelating agent that occurs in nature, i.e. not an agent that has been first synthesized by human intervention. The naturally occurring chelating agent may be a low molecular weight chelating agent, where by low molecular weight chelating agent is meant that the molecular weight of the chelating agent does not exceed about 200 daltons. In certain embodiments, the molecular weight of the chelating agent is greater than about 100 daltons.

Naturally occurring low molecular weight chelating agents that may be used are microbial produced chelating agents, where by "microbial produced" is meant that the chelating agent is produced by a microbe, where the microbe is generally a bacterium or a fungus. In many embodiments, the chelating agents are citric acid cycle intermediates and derivatives thereof. Specific chelating agents of interest include: malic acid, succinic acid, oxalacetic acid, ketoglutaric acid and citric acid and amino acids derived from citric acid cycle intermediates, such as glycine (75.1 daltons), alanine (89.1 daltons), serine (105.1 daltons), valine (117.2 daltons), threonine (119.1 daltons), cysteine (121.2 daltons), leucine (131.2 daltons), isoleucine (131.2 daltons), aspargi- nine (132.1 daltons), glutamine (146.2 daltons), methionine (149.2 daltons), etc. Accordingly, embodiments include compositions that may include a source of at least one naturally occurring chelating agent. By source is meant that the compositions may include the chelating agents or an entity or component that produces the chelating agents. In many embodiments, the source of chelating agents is a living or viable microbial source of chelating agents. For example, the microbial source may be a bacterial or fungal culture which produces the requisite chelating agents.

The total amount of complexing agent present in a given composition (whether one or a plurality of complexing agents) depends on a variety of factors such as the particular plant to which the composition is to be administered, the particular complexing agent(s) employed, and the like. In certain embodiments, the total amount of complexing agent in the composition may range from about 0.01% to about 5% w/w, e.g., from about 0.1% to about 4.5% w/w, e.g., from about 1.0% to about 4% w/w.

Exotic Micronutrient Component

As noted above, compositions include one or more sources of extracted humate. In embodiments of the invention, the one or more sources of extracted humate serves as a combined complexing agent and source of exotic micronutrient. Exotic micronutrients of the subject compositions include a set or collection of non-traditional micronutrients, where the non-traditional micronutrients may be ones that provide ionic elements found in low amounts, e.g., low parts per million to parts per billion range, in virgin soils (i.e., soils that have not been used previously for agriculture). For example, non-traditional micronutrients may be micronutrients that promote the electrostatic bonding of amino acid chains. As such, powder or fine forms of oxidized coal, oxidized bituminous material, ironite, volcanic rock, shale, fossilized peat, moss, kelp or seaweed find use in the subject compositions to provide a source of one or more exotic micronutrients.

A given source of extracted humate provides at least one distinct exotic micronutrient ionic element. In some embodiments, the source of extracted humate may provide for 5 or more distinct exotic micronutrient ionic elements, such as 10 or more distinct exotic micronutrient ionic elements, such as 20 or more distinct exotic micronutrient ionic elements, such as 30 or more distinct exotic micronutrient ionic elements, such as 40 or more distinct exotic micronutrient ionic elements and including 50 or more distinct exotic micronutrient ionic elements.

Exotic micronutrient ionic elements of interest include, but are not limited to: Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium(Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silica (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

It is noted that sulfur is listed as a possible exotic micronutrient and yet also listed as a possible macronutrient above. In embodiments where the one or more sources of extracted humate include sulfur, sulfur will not be additionally included as a macronutrient. It is further noted that boron, molybdenum and cobalt are all listed as possible exotic micronutrients and yet are also listed as a possible micronutrients above. In embodiments where the one or more sources of extracted humate includes boron, molybdenum and cobalt, these elements will not be present additionally included as micronutrients.

Exotic micronutrients provided by the one or more sources of extracted humate may be present in the form of salts which provide for the desired ionic elements. Examples of sources salts are summarized in Table 1:

TABLE 1

| Exotic Micronutrient Element | Symbol | Source: Nitrates | Source: Chlorides | Source: Sulfides | Source: Oxides | Source: Misc. |
|---|---|---|---|---|---|---|
| Europium | Eu | $Eu(NO_3)_3$ | $EuCl_3$ | $Eu_2(SO_4)_3$ | $Eu(OH)_3$ $Eu_2O_3$ | |
| Fluorine | F | $FNO_3$ | | | $F_2O$ | $C_2H_4FNO$: Fluoroacetamide $C_2H_3FO_2$: |

TABLE 1-continued

| Exotic Micronutrient Element | Symbol | Source: Nitrates | Source: Chlorides | Source: Sulfides | Source: Oxides | Source: Misc. |
|---|---|---|---|---|---|---|
| | | | | | | Fluoroacetic Acid ClFO$_4$: Perchlorate |
| Gadolinium | Gd | Gd(NO$_3$)$_3$ | GdCl$_3$ | Gd$_2$(SO$_4$)$_3$ | Gd(OH)$_3$ Gd$_2$O$_3$ | |
| Gallium | Ga | Ga(NO$_3$)$_3$ | GaCl$_3$ | Ga$_2$(SO$_4$)$_3$ | Ga(OH)$_3$ Ga$_2$O$_3$ | |
| Germanium | Ge | | Cl$_2$Ge Cl$_4$Ge | | GeO$_2$ | F$_4$Ge: Tetrafluoride |
| Gold | Au | | AuCl | Au$_2$S | Au$_2$O | CAuN: Monocyanide AuI: Monoiodide |
| Hafnium | Hf | | HfCl$_4$ | Hf(SO$_4$) | HfO$_2$ | |
| Holmium | Ho | | HoCl$_3$ | | Ho$_2$O$_3$ | HoB$_3$: Bromide HoI$_3$: Iodide |
| Indium | In | | Cl$_3$In | In$_2$O$_{12}$S$_3$ | In$_2$O$_3$ | InP: Phosphide AsIn: Arsenide |
| Lanthanum | La | La(NO$_3$)$_3$ | LaCl$_3$ | La$_2$(SO$_4$)$_3$ | La(OH)$_3$ La$_2$O$_3$ | |
| Lithium | Li | LiNO$_3$ | ClLi | Li$_2$O$_4$S | HLiO Li$_2$O | |
| Lutetium | Lu | | LuCl$_3$ | Lu$_2$(SO$_4$)$_3$ | Lu$_2$O$_3$ | |
| Neodymium | Nd | Nd(NO$_3$)$_3$ | NdCl$_3$ | Nd$_2$(SO$_4$)$_3$ | Nd(OH)$_3$ Nd$_2$O$_3$ | |
| Nickel | Ni | N$_2$NiO$_6$ | Cl$_2$Ni | NiO$_4$S | H$_2$NiO$_2$ Ni$_2$O$_3$ | |
| Niobium | Nb | | Cl$_5$Nb | | Nb$_2$O$_5$ | F$_4$Nb Pentafluoride F$_7$K$_2$NbO Oxypenafluoride |
| Platinum | Pt | na | na | na | na | |
| Praseodymium | Pr | | PrCl$_3$ | Pr$_2$(SO$_4$)$_3$ | Pr(OH)$_3$ PrO$_2$ Pr$_2$O$_3$ | |
| Rhodium | Rh | | C$_4$Cl$_2$O$_4$Rh$_2$ Cl$_3$Rh | | | |
| Ruthenium | Ru | | Cl$_3$Ru Cl$_6$H$_{42}$N$_{14}$O$_2$Ru | | O$_4$Ru | |
| Samarium | Sm | | SmCl$_2$ SmCl$_3$ | Sm$_2$(SO$_4$)$_3$ | Sm(OH)$_3$ Sm$_2$O$_3$ | |
| Scandium | Sc | Sc(NO$_3$)$_3$ | ScCl$_3$ | Sc$_2$(SO$_4$)$_3$ | Sc(OH)$_3$ O$_3$Sc$_2$ | |
| Silicon | Si | | Cl$_4$Si | S$_2$Si: Disulfide | OSi O$_2$Si | F$_4$Si: Tetrafluoride CSi: Carbide Br$_4$Si: Tetrabromide |
| Silver | Ag | AgNO$_2$ Ag(NO$_3$)$_3$ | AgCl AgClO$_4$ | Ag$_2$S Ag$_2$O$_4$S | AgO Ag$_2$O C$_2$Ag$_2$O$_4$ | AgI: Iodide AgF: Fluoride |
| Strontium | Sr | N$_2$O$_6$Sr | Cl$_2$Sr Cl$_2$O$_6$Sr | O$_4$SSr | OSr O$_2$Sr H$_2$O$_2$Sr | F$_2$Sr: Floride |
| Sulfur | S | | Cl$_2$S$_2$ Cl$_2$O$_2$S | | O$_2$S O$_3$S | H$_2$O$_4$S: Sulfuric Acid SI: Iodide F$_4$S: Tetrafluoride |
| Tellurium | Te | | Cl$_2$Te Cl$_4$Te | | O$_2$Te | Br$_2$Te: Tetrabromide F$_6$Te: Tetrafluoride H$_2$O$_3$Te: Telluric Acid |
| Terbium | Tb | Tb(NO$_3$)$_3$ | TbCl$_3$6H$_2$O | | O$_3$Tb$_2$ Tb$_4$O$_7$ | |
| Thallium | Tl | NO$_3$Tl | Cl$_3$Tl | STl$_2$ O$_4$STl$_2$ | HOTl OTl$_2$ | C$_2$H$_3$O$_2$Tl: Acetate |
| Thorium | Th | N$_4$O$_{12}$Th | Cl$_4$Th | O$_8$S$_2$Th | O$_2$Th | I$_4$Th: Iodide |
| Thulium | Tm | Tm(NO$_3$)$_3$ | TmCl$_3$.7H$_2$O | Tm$_2$(SO$_4$)$_3$.8H$_2$O | Tm(OH)$_3$ O$_3$TM$_2$ | Tm$_2$(C$_2$O$_4$)$_3$.6H$_2$O: OOxalate hexahydrate |
| Tin | Sn | | | | SnO | Sn$_4$P$_3$: Phosphides |
| Titanium | Ti | | C$_{10}$H$_{10}$Cl$_2$Ti Cl$_2$Ti Cl$_3$Ti Cl$_4$Ti | O$_5$STi O$_{12}$S$_3$Ti$_2$ | O$_2$Ti | F$_4$Ti: Tetrafluoride H$_2$Ti: Hydride |

TABLE 1-continued

| Exotic Micronutrient Element | Symbol | Source: Nitrates | Source: Chlorides | Source: Sulfides | Source: Oxides | Source: Misc. |
|---|---|---|---|---|---|---|
| Tungsten | W | | | | $O_3W$ | $F_6W$: Hexafluoride<br>$H_2O_4W$: Tungstic Acid |
| Vanadium | V | | $Cl_2OV$<br>$Cl_3OV$ | $O_6SV$<br>$S_3V_2$<br>$O_{12}S_3V_2$ | $O_3V_2$<br>$O_5V_2$ | $F_3V$: Trifluoride<br>$F_4V$: Tetrafluoride<br>$F_5V$: Pentafluoride |
| Ytterbium | Yb | $Yb(NO_3)_3$ | $YbCl_3$ | $Yb_2(SO_4)_3$ | $O_3Yb_2$ | |
| Yttrium | Y | $Y(NO_3)_3$ | $YCl_3$ | $Y_2(SO_4)_3$ | $O_3Y_2$<br>$Y(OH)_3$ | |
| Zirconium | Zr | $N_4O_{12}Zr$ | $Cl_4Zr$<br>$Cl_2OZr$ | $O_8S_2Zr$ | $O_2Zr$<br>$H_4O_4Zr$ | $ZrF_4$: Tetrafluoride<br>$ZrH_2$: Hydride<br>$I_4Zr$: iodide |

The above list of sources of the exotic micronutrients provided by the one or more sources of extracted humate are merely representative.

The overall amount of exotic micronutrient present in extracted humate, may vary where in certain embodiments, the amount ranges from 0.001 ppb to 100 ppb w/w, such as 0.005 ppb to 75 ppb w/w, such as 0.01 ppb to 50 ppb w/w, such as 0.05 ppb to 25 ppb w/w and including 0.01 ppb to 10 ppb w/w.

The amounts of individual exotic micronutrients may be chosen to provide for concentrations of elements as desired, where the desired concentrations of elements may vary, depending on the particular nature of the exotic micronutrient. For example, one class of exotic micronutrients may be viewed as "severe" micronutrients, and includes Hg (Mercury), Cd (Cadmium), Cs (Cesium). The amounts of these micronutrients may be chosen to provide a concentration in the concentrated product ranging from 1 to 10 ppb, such as 7.5 ppb. Another class of exotic micronutrients may be viewed as "intermediate" micronutrients, and includes Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium). The amounts of these micronutrients may be chosen to provide a concentration in the concentrated product ranging from 10 to 25 ppb, such as 15 ppb. Another class of exotic micronutrients may be viewed as "Standard I" micronutrients, and includes Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium). The amounts of these micronutrients may be chosen to provide a concentration in the concentrated product ranging from 20 to 40 ppb, such as 35 ppb. Another class of exotic micronutrients may be viewed as "Standard II" micronutrients, and includes Bi (Bismuth), Eu (Europium), Ho (Holmium), Nd (Neodymium), Pt (Platinum), Ag (Silver), Tl (Thallium), Th (Thorium). The amounts of these micronutrients may be chosen to provide a concentration in the concentrated product ranging from 95 to 150 ppb, such as 90 ppb. Another class of exotic micronutrients may be viewed as "Standard III" micronutrients, and includes Br (Bromine), F (Fluorine), Au (Gold), In (Indium), Pr (Praseodymium), Tb (Terbium), Tm (Thulium). The amounts of these micronutrients may be chosen to provide a concentration in the concentrated product ranging from 400 to 1,000 ppb, such as 850 ppb. Another class of exotic micronutrients may be viewed as "Standard IV" micronutrients, and includes Nb (Niobium), Sc (Scandium), Si (Silicon), S (Sulfur), Y (Yttrium). The amounts of these micronutrients may be chosen to provide a concentration in the concentrated product ranging from 2,000 to 3,700 ppb, such as 3,200 ppb.

An embodiment of the an exotic micronutrient component of interest is one that provides ionic species of the following elements in the amounts provided below: (1) Hg (Mercury), Cd (Cadmium), and Cs (Cesium) ranging from 1 to 10 ppb, such as 7.5 ppb; (2) Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium) ranging from 10 to 25 ppb, such as 15 ppb; (3) Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium) ranging from 20 to 40 ppb, such as 35 ppb; (4) Bi (Bismuth), Eu (Europium), Ho (Holmium), Nd (Neodymium), Pt (Platinum), Ag (Silver), Tl (Thallium), Th (Thorium) ranging from 95 to 150 ppb, such as 90 ppb; (5) Br (Bromine), F (Fluorine), Au (Gold), In (Indium), Pr (Praseodymium), Tb (Terbium), Tm (Thulium) ranging from 400 to 1,000 ppb, such as 850 ppb; and (6) Nb (Niobium), Sc (Scandium), Si (Silicon), S (Sulfur), Y (Yttrium) ranging from 2,000 to 3,700 ppb, such as 3,200 ppb.

Ionophore Component

Compositions of interest also include an ionophore. The term "ionophore" is used in its conventional sense to refer to the class of organic compounds that are capable of transporting ions across lipid barriers in a plant cell. Ionophores of interest include, but are not limited to antibiotics, such as Gramicidin A and Valinomycin, and Amino Butyric Acids (ABA), such as D-alpha ABA, DL-alpha ABA, L-alpha ABA, DL-Beta ABA, Gama-ABA (GABA) (e.g., 4-GABA), and the like.

The total amount of ionophore in the subject compositions may range from about 10 ppm to 500 ppm w/w, such as 25 ppm to 450 ppm w/w, such as 50 ppm to 400 ppm w/w, such as 75 ppm to 350 ppm w/w, such as 100 ppm to 300 ppm and including 150 ppm to 250 ppm w/w, for example 200 ppm w/w.

Flowing Agent

As discussed above, the subject compositions for enhancing pollination are dry composition, such that they include 1% w/w water or less, such as 0.5% w/w water or less, such as 0.1% w/w water or less, such as 0.05% w/w water or less, such as 0.01% w/w water or less, such as 0.005% w/w water or less and including 0.001% w/w water or less. As such, compositions of the invention are solid compositions provided in fine grain or powder form. Atmospheric moisture, pressure and temperature can each adversely affect powdered and granulated compositions. These conditions can make compositions cake, lump, bridge, clog application equipment and cause packaging and problems with uptake by the subject flora. Accordingly, in some embodiments, the subject dry compositions further include a flowing agent. By "flowing agent" is meant one or more compounds which facilitate the uninterrupted flow of the powdered composition with minimal hang up on the walls of a container. Flowing agents of interest include, but are not limited to corn starch, sifted wheat flour, sifted corn flour, sifted rice flour, commercial anti-caking agents, silica-based anti-caking agents, hygroscopic absorption agents and the like.

Depending on components in the composition, the particle size of the flowing agent may vary, so long as it is sufficient to provide uninterrupted flow and minimal hang up on the walls of the container when applying the composition to the subject flora. For example, the particle size may vary ranging from 0.01 μm to 100 μm, such as from 0.1 μm to 75 μm, such as from 1 μm to 50 μm, such as from 2.5 μm to 25 μm and including from 5 μm to 10 μm.

The total amount of flowing agent in the subject compositions may range from about 10% to 40% w/w, such as 15% to 35% w/w, such as 20% to 30% w/w and including 22.5% to 27.5% w/w.

Source of Protein

As described in greater detail below, in certain embodiments the subject compositions are employed as a food supplement to enhance pollination, such as for example where the honey bee is the subject biotic vector in cross-pollination. In these embodiments, compositions of interest may further include a source of protein. The source of protein may be any convenient complex amino acids, such as for example soy powder, milled barley, milled corn meal, powdered milk and pollen.

The total amount of protein in the subject compositions may range from about 5% to 75% w/w, such as 10% to 70% w/w, such as 15% to 60% w/w, such as 25% to 50% and including 30% to 40% w/w.

Pollen

In certain embodiments, the subject compositions further include pollen. The term "pollen" is used in its conventional sense to refer to the fine to coarse powder containing the microgametophytes of seed plants. The pollen incorporated into the subject compositions may be any type of pollen, as desired. In certain embodiments, the pollen in compositions of interest is pollen which has been obtained from the same type of plant as the subject flora. For example, in certain embodiments, when the pollination enhancing compositions of the invention are applied over almond orchards, pollen incorporated into the subject compositions includes almond blossom pollen. In certain instances, the pollen is pollen which is obtained directly from the plants which will be applied with the subject compositions. The pollen may be obtained at a predetermined amount of time prior to application of the subject compositions to the target flora. For example, the pollen may be obtained 1 hour or more prior to application to the target flora, such as 2 hours or more, such as 3 hours or more, such as 6 hours or more, such as 12 hours or more, such as 24 hours or more and including 168 hours or more prior to application to the target flora. In certain In other instances, the pollen is obtained from blossoms of one or more prior seasons.

Where the subject compositions include a pollen component, the pollen component may include pollen from one or more different types of plants, such as 2 or more, such as 3 or more, such as 4 or more, such as 5 or more and including 10 different types of plants. In one example, the pollen component is pollen from a single type of plant, such as where the pollen is from the same type of plant as the target flora. In another example, the pollen component is a pollen blend having a mixture of pollen from two or more different types of plants.

In some embodiments, the pollen includes only pure pollen grains. By "pure pollen" is meant that the pollen includes substantially only the grains of pollen and do not include anther sacs, filaments, chaff from flowers and other impurities which may be found in pollen obtained by traditional pollen harvesting. Accordingly, where the pollen component includes pure pollen grains, the pollen component include an amount of pollen grains that is 99% w/w or greater of the pollen component, such as 99.5% w/w or greater pollen grains, such as 99.7% w/w or greater pollen grains, such as 99.9% w/w or greater pollen grains and including 99.99% w/w or greater pollen grains. In other words, pure pollen includes impurities in an amount of 1% w/w or less, such as 0.5% w/w or less, such as 0.3% w/w or less, such as 0.1% w/w or less and including impurities in an amount of 0.01% or less. Where the subject compositions include pure pollen grains, pollen may be initially processed (as described below), such as to remove any anther sacs, filaments, chaff from flowers and other impurities to produce the pure pollen grains.

As described in greater detail below, in certain embodiments the subject compositions are employed as a food supplement to improve the nutrition of targeted biotic vectors, increase activity by the biotic vector or to increase the specificity of a target biotic vector for the subject flora.

The total amount of pollen in the subject compositions may range from about 1% w/w to 25% w/w, such as 2% w/w to 22.5% w/w, such as 3% w/w to 20% w/w, such as 5% w/w to 15% w/w and including 5% w/w to 10% w/w.

Methods for Enhancing Pollination

As summarized above, aspects of the invention also include methods for enhancing pollination by applying the subject compositions to the foliage of one or more plants. By enhancing pollination the overall effective cross pollination by biotic vectors is increased such that a greater number of subject flora are pollinated when applied with compositions of interest as compared to flora that is not applied with the subject compositions. For example, in some instances methods of the invention include increasing effective cross pollination by 5% or more, such as by 10% or more, such as by 25% or more, such as by 50% or more, such as by 75% or more, such as by 90% or more, such as by 95% or more and including by 100% or more as compared to flora not applied the subject compositions. In other instances, methods of the invention include increasing effective cross pollination by 1.5-fold or greater, such as 2-fold or greater, such as 2.5-fold or greater, such as 3-fold or greater, such as 5-fold or greater and including increasing effective cross pollination by 10-fold or greater.

Alternatively, enhancing pollination may be realized by a particular goal, where in some instances the desired enhancement is an increase in cross pollination that ultimately results in greater production of some desirable parameter, such as for example the amount of harvested crop produced by the subject flora. For example, methods of the invention may enhance pollination by increasing the amount of harvested crop by 10% or more, such as 25% or more, such as 50% or more, such as 75% or more and including increasing the amount of harvested crop by 100% or more. In other instances, methods of the invention may increase harvested crop production by 1.5-fold or greater, such as 2-fold or greater, such as 2.5-fold or greater, such as 3-fold or greater, such as 5-fold or greater and including increasing harvested crop production by 10-fold or greater. For instance, where the harvested crop are fruits, nuts or vegetables methods for enhancing pollination may increase the amount of crop produced by 250 pounds per acre or more, such as 500 pounds per acre or more, such as 1000 pounds per acre or more, such as 1500 pounds per acre or more and including by 2000 pounds per acre or more.

In embodiments of the invention, methods include contacting the foliage of plant(s) with one or more of the subject compositions as described above. By contacting is meant that an amount of the dry composition is placed on the surface of the foliage of the plant(s) to be treated. The term "foliage" is used herein to refer to all parts of the plant which are above ground, i.e. above the soil surface, where the term "foliage" may include leaves, stems, flowers, fruit, etc. As such, methods may include applying one or more of the dry pollination enhancing compositions described above to at least one of the leaves, stems, flowers or fruit of subject flora. The subject flora may be any type of plant which would benefit from enhanced pollination. As such, plants may include fruit-trees, nut-trees, grain crops, legumes, fruit vines, squash vines, flowering vegetables, among other types of plants. For example, flora of interest for enhanced pollination may include, but is not limited to crop plants for almonds, kiwifruit, okra, bucket orchid, onion, scallion, cashews, cherimoya, celery, strawberry, American pawpaw, starfruit, brazil nut, beet, mustard, rapeseed, broccoli, cauliflower, cabbage, Brussels sprouts, turnip, beans, chili peppers, bell peppers, papaya, safflower, caraway, chestnut, star apple, watermelon, tangerine, tangelo, coconut, coffee, cola nut, coriander, crownvetch, hazelnut, azarole, cantaloupe, cucumber, squash, pumpkin, zucchini, gourd, guar bean, quince, lemon, lime, orange, carrot, grapefruit, pomelo, hyacinth bean, longan, lychee, persimmon, durian, oil palm, cardamom, loquat, kumquat, buckwheat, feijoa, fig, fennel, soybean, stanhopea, cotton, sunflower, walnut, flax, lupine, macadamia, acerola, apple, mammee apple, mango, sapodilla, alfalfa, rambutan, cactus, prickly pear, sainfoin, passion fruit, avocado, lima bean, kidney bean, string beans, green beans, mung beans, red beans, black beans, pinto beans, allspice, apricot, cherry, plum, peach, nectarine, guava, pomegranate, pear, currant, rose hips, boysenberry, raspberry, blackberry, blueberry, elderberry, cranberry, sesame, eggplant, naranjillo, rowanberry, hog plum, tamarind, cocoa, clover, vanilla, tung tree, vetch, cowpea, black-eyed peas, karate, tomato, grape, dragonfruit, jujube, among other crop plants.

In embodiments of the invention, an amount of one or more of the pollination enhancing compositions described above is contacted with the foliage of a plant(s). The composition may be contacted with the foliage by any convenient protocol. In some embodiments, compositions are contacted with foliage by aerial application. Aerial application may include, but is not limited to spraying, dusting and otherwise applying the subject compositions by agricultural aircraft, crop-dusting airplanes, gliders, helicopters, ultra-lights, biplanes, remote control airplanes, as well as motorized, mechanically or electrically powered sprayers or dusters supported by an elevated apparatus (e.g., towers, hydraulic lifts, cranes or support columns). In other embodiments, compositions may be contacted with the foliage of subject flora on the ground using motorized, mechanically or electrically powered applicators, such as a tractor or other agricultural vehicle equipped with a sprayer, duster or blower or by hand-held sprayers, blowers, dusters and the like. Compositions may alternatively be manually applied (i.e., by hand). In certain embodiments, the composition is applied to the foliage of subject flora using a hand-held duster with squirrel cage fan.

The amount of the dry composition employed during any single application may vary depending on the number of plants, size of the plants, geographical area and environmental conditions (e.g., wind conditions, precipitation, etc.). Any amount may be applied so long as the amount is sufficient to enhance pollination as desired. In some embodiments, the amount applied per acre may range from about 0.01 to 10 pounds per acre, such as 0.05 to 9 pounds per acre, such as 0.1 to 8 pounds per acre, such as 0.5 to 7 pounds per acre, such as 1 to 6 pounds per acre and including 2 to 5 pounds per acre. Depending on the type of subject flora, environmental conditions, and desired amount of enhanced pollination, the subject compositions may be applied periodically (i.e., in predetermined time intervals). As such, the composition may be applied daily, weekly, every two weeks, monthly etc. In certain embodiments, the subject compositions are applied twice during bloom. Alternatively, the subject compositions may be simply applied as needed, where enhanced pollination has been determined to be necessary or desired by a trained agriculturalist or apiculturist.

Methods may include a single application of the subject compositions or may include multiple application intervals. By "multiple application intervals" is meant more than a single application of the composition, i.e., one or more subsequent application of the composition is performed after the first application. In practicing methods of the invention, enhanced pollination protocols may include two or more application intervals, such as three or more application intervals, such as four or more application intervals and including five or more application intervals.

The duration between application intervals may vary depending on the size and number of plants, geographical location, environmental conditions, size, number of the source of biotic vectors, type of biotic vector, etc. In certain instances, the duration between application intervals may be predetermined and follow at regular intervals. For example, the time between application intervals may be 1 hour or longer, such as 2 hours or longer, such as 5 hours or longer, such as 10 hours or longer, such as 12 hours or longer, such as 24 hours or longer, such as 48 hours or longer, such as 72 hours or longer, such as 96 hours or longer and including 168 hours or longer. Alternatively, the time between application intervals may be on demand, where one or more subsequent applications is performed based on need determined by a trained agriculturalist or apiculturist.

In some embodiments, methods of enhancing pollination include increasing the number of biotic vectors which visit plants applied with the subject compositions. As described above, biotic vectors of the invention may be any pollen carrying organism which moves pollen from the male anthers to the female stigma of a flower to accomplish syngamy of the female gamete in the ovule of a flower by the male gamete in the pollen. Biotic vectors may include, but are not limited to insects such as bees, honeybees, bumblebees, orchard mason bees, leaf cutter bees, bluebottle flies, wasps, bee flies, butterflies, moths, beetles, flies, midges, thrips, fruit flies, horse flies and vertebrates, such as bats, hummingbirds, honeyeaters, sunbirds, among other types of pollinators. For example, the number of biotic vectors (e.g., honeybees) which visit the flora applied with the subject compositions may be increased by 10% or greater as compared to the number of biotic vectors which visit plants which have not been applied with compositions of interest, such as 15% or greater, such as 25% or greater, such as 35% or greater, such as 50% or greater, such as 65% or greater, such as 75% or greater, such as 90% or greater, such as 95% or greater, such as 99% or greater and including 100% or greater as compared to the number of biotic vectors which visit flora which has not been applied with the subject compositions. In other instances, the number of biotic vectors which visit plants applied with the subject compositions may be increased by 1.5-fold or greater as compared to the number of biotic vectors which visit flora which has not been applied with compositions of interest, such as 2-fold or greater, such as 2.5-fold or greater, such as 3-fold or greater, such as 4-fold or greater, such as 5-fold or greater, such as 10-fold or greater, such as 25-fold or greater and including 100-fold or greater as compared to the number of biotic vectors which visit flora which has not been applied with compositions of interest. In these embodiments, methods may further include surveying (e.g., counting) the number of biotic vectors which visit the subject flora prior to and following application of compositions. Surveying may include monitoring by human observation or electronic surveillance (e.g., video) alone or with the assistance of a computer to determine the absolute or approximate number of biotic vectors which visit a given area of subject flora prior to and after applying compositions of the invention. The increase in biotic vectors which visit plants applied with the subject compositions may be determined at a predetermined time after applying the subject compositions, such as after 10 minutes, 30 minutes, 1 hour, 2 hours, 3 hours, 5 hours, 10 hours, 12 hours, 24 hours, 48 hours and including surveying the number of biotic vectors 72 hours after applying the subject compositions. Alternatively, surveying for the number of biotic vectors which visit plans applied with the subject compositions may be performed periodically such as every hour or more, such as every 2 hours or more, such as every 3 hours or more, such as every 5 hours or more, such as every 10 hours or more, such as every 12 hours or more, such as every 24 hours or more, such as every 48 hours or more and including every 72 hours or more.

In some embodiments, methods include employing one or more of the subject compositions as a nutritional supplement or food for a biotic vector. For example, the subject composition may be a bee food supplement to increase the activity and health of the honeybees used in pollination. The compositions may be contacted with the biotic vectors by any convenient protocol, such as those described above for applying to the foliage of one or more plants (e.g., spraying or applying using a hand-held applicator, backpack mounted duster or blower). The subject compositions may be contacted with the source of biotic vectors, such as directly at the entrance of beehive, wasp nest, hummingbird nest, etc. The composition may be contacted with the target biotic vectors, as desired, where in certain embodiments, the compositions are contacted with a source of biotic vectors at a predetermined time before allowing the biotic vectors to visit the subject flora. For example, compositions may be contacted with a source of biotic vectors 10 minutes prior to allowing the biotic vectors to visit subject flora, such as 30 minutes, such as 1 hour, such as 2 hours, such as 3 hours, such as 5 hours, such as 10 hours, such as 12 hours, such as 24 hours, such as 48 hours and including 72 hours before allowing the biotic vectors to visit the subject flora. Any amount may be fed to biotic vectors, as desired. In some embodiments, the amount applied per source of biotic vector (e.g., per beehive) may range from about 0.001 to 10 pounds per source, such as 0.005 to 9 pounds per source, such as 0.01 to 8 pounds per source, such as 0.05 to 7 pounds per source, such as 0.1 to 6 pounds per source and including 1 to 5 pounds per source.

In certain embodiments, methods include applying an amount of one or more of the subject compositions to plants in combination with applying an amount of the subject composition to one or more sources of biotic vectors (e.g., honeybee hive). Where an amount of the composition is applied to subject flora and one or more sources of biotic vectors, the composition applied to the subject flora and the source of biotic vector may be the same or different. For example, a first composition may be applied to the subject flora while a second, different composition may be applied to the source of biotic vectors. Alternatively, a first composition may be applied to both the subject flora and source of biotic vectors. Application to the subject flora and source of biotic vectors can be simultaneous or performed at different times (i.e., sequentially, in either order, on the same day, or on different days).

Where the subject compositions are applied to a biotic vector in combination with the subject flora, the compositions may further include pollen. As described above, the pollen may be any type of pollen, as desired. In certain embodiments, the pollen is pollen which has been obtained from the same type of plant as the subject flora. For example, in certain embodiments, when the pollination enhancing compositions of the invention are applied over almond orchards, pollen incorporated into the subject compositions includes almond blossom pollen. In certain instances, the pollen is pollen which is obtained directly from the plants which will be applied with the subject compositions. The pollen may be obtained at a predetermined amount of time prior to application of the subject compositions to the target flora. For example, the pollen may be obtained 1 hour or more prior to application to the target flora, such as 2 hours or more, such as 3 hours or more, such as 6 hours or more, such as 12 hours or more, such as 24 hours or more and including 168 hours or more prior to application to the target flora. In certain instances, the pollen is obtained from blossoms of one or more prior seasons.

As such, methods of the invention may further include obtaining pollen from the subject flora. Pollen may be obtained using any convenient protocol, such as by a mechanical, motorized or electrical pollen harvesting apparatus. Alternatively, the pollen may be manually (i.e., by hand) harvested. The pollen component may include pollen obtained from one or more different types of plants, such as 2 or more, such as 3 or more, such as 4 or more, such as 5 or more and including 10 different types of plants. In one example, the pollen component is pollen obtained from a single type of plant, such as where the pollen is obtained from the same type of plant as the target flora. In another example, the pollen component is a pollen blend having a mixture of pollen obtained from two or more different types of plants.

Accordingly in these embodiments, an amount of the subject compositions is applied to the foliage of one or more plants in combination with applying an amount of the composition to a source of biotic vectors. For example, an amount of a composition having a carbon skeleton energy compound (CSE), macronutrients, a vitamin cofactor composition, micronutrients, an ionophore, pollen obtained from the subject flora and one or more sources of extracted humate may be simultaneously or sequentially applied to the foliage of a fruit-tree, nut-tree or flowering vegetables while applying the composition to a honeybee hive.

In certain embodiments, methods include determining that subject flora is in need of enhanced pollination. Determining that subject flora is in need of enhanced pollination may be performed by any convenient protocol, such as determined by a trained professional agriculturalist or apiculturist. In practicing methods of the invention, determining whether subject flora is in need of enhanced pollination may include assessing the subject flora and evaluating by a human (either alone or with the assistance of a computer, if using a computer-automated program initially set up under human direction) whether the subject flora would benefit from enhanced pollination.

In some instances, the subject flora may be determined to be in need of enhanced pollination where the subject flora has shown a 5% or greater decrease in crop production as compared to a suitable control (e.g., previous seasons production), such as a 10% or greater decrease in crop production, such as a 15% or greater decrease in crop production, such as a 20% or greater decrease in crop production and including a 25% or greater decrease in crop production as compared to a suitable control.

In other instances, the subject flora may be determined to be in need of enhanced pollination where the subject flora has a crop production per area (e.g., pounds of fruits, nuts, vegetables, etc. per acre) which is below a predetermined threshold. For example, the subject flora may be determined to be in need of enhanced pollination where the crop production per area is 2% or greater below a predetermined threshold, such as 3% or greater below, such as 4% or greater below, such as 5% or greater below and including 10% or greater below a predetermined threshold.

In yet other instances, the subject flora may be determined to be in need of enhanced pollination where the number of biotic vectors found in a given area of the subject flora is below a predetermined threshold. For example, an area of subject flora may be surveyed for the number of biotic vectors found per area (e.g., number of honeybees per square acre) and where the number of biotic vectors surveyed is 1% or greater below a predetermined threshold, the area of subject flora is determined to be in need of enhanced pollination. For instance, subject flora may be determined to be in need of enhanced pollination where the number of biotic vectors found per area is 2% or greater below a predetermined threshold, such as 3% or greater below, such as 4% or greater below, such as 5% or greater below and including 10% or greater below a predetermined threshold.

Determining whether subject flora is in need of enhanced pollination may be performed at any time as desired. For example, determining whether subject flora is in need of enhanced pollination may be performed at predetermined intervals such as every day, every week, every two weeks, every month, etc. Alternatively, determining whether the subject flora is in need of enhanced pollination may be performed in conjunction with methods for applying the subject compositions as described above. For example, the subject flora may be monitored by human observation or electronic surveillance (e.g., video), between intervals during a multiple application interval and evaluated whether the subject flora is in need of subsequent application intervals. The subject flora may be evaluated for need of enhanced pollination 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions.

According to certain aspects, methods further include preparing pollen grains suitable for use in the subject composition. In certain embodiments, methods for preparing pollen grains are characterized by a first process of separating pollen grains from floral blossoms and a second process of preparing the separated pollen grains for use in the subject compositions. In some instances, methods for preparing pollen grains may include a first process where pollen-containing anthers are separated from floral blossoms and other plant material, such as filaments, petals and chaffs; separating viable anthers from non-viable anthers; dislodging pollen grains from the separated viable anthers and separating dislodged pollen grains from the viable anthers. In some instances, methods for preparing pollen grains may further include a second process where the separated pollen grains are dried, sorted and collected for use in the subject compositions.

In embodiments, methods for preparing pollen grains include separating anthers from floral blossoms of interest. Anthers may be separated from the floral blossoms by any convenient separation protocol, such as but not limited to shredders, revolving cylinders, blenders, agitators, blossom trimmers, rotary separators among other separation protocols, such as for example manually ((i.e., by hand) separating anthers from the floral blossoms. In certain embodiments, the floral blossoms are placed through a low speed rotary shredder, where cutting teeth are replaced by two parallel cylinders revolving to direct flow of the separated anthers inward. In these embodiments, the cylinders may be equipped with sheet metal screws (flat tipped with spiral groove on the shaft) which extend from the inside of the cylinder wall to the periphery. The axis of the sheet metal screws pass directly through and are perpendicular to the central axis of the revolving cylinder. Gentle flailing by the cutting teeth dislodge mature anthers from the floral blossoms.

Anthers separated from floral blossoms of interest are, in some embodiments, further sorted to separate anthers containing viable pollen from anthers containing non-viable pollen. The term "viable" is used in its conventional sense to refer to the capacity of the pollen to live, grow, fertilize, germinate or develop, such as being capable of germinating on the stigma (i.e., germinability) or being capable of fertilization (i.e., fertility). The viability of pollen can be determined using any convenient protocol, including but not limited to staining, in vitro culture, in situ germination and visual inspection. In one example, anthers may be determined as containing non-viable pollen by visual inspection, such as by observing dehisced anthers. In another example, anthers may be determined as containing viable pollen by staining, such as by employing Alexander's stain or tetrazolium red vital stain. Anthers containing viable pollen and anthers containing non-viable pollen may be separated by any convenient separation protocol, including but not limited to revolving cylinders, blenders, agitators, rotary separators, sifters, multi-level shakers, among other separation protocols, such as for example manually ((i.e., by hand) separating anthers containing viable pollen from anthers containing non-viable pollen. In certain embodiments, anthers (e.g., dehisced) containing non-viable pollen are separated from anthers containing viable pollen on a shaking deck having three levels: a top, coarse mesh stainless steel screen; a middle fine mesh stainless steel screen and a bottom basin. Depending on the source of anthers (e.g., almond blossoms, cherry blossoms, etc.), the size of the coarse mesh may vary, such as from 2 to 100, such as from 5 to 90 mesh, such as from 10 to 75 mesh, such as from 15 to 60 mesh and including from 25 to 50 mesh. Likewise, the mesh size of the fine mesh may vary, such as from 50 to 400 mesh, such as from 75 to 375 mesh, such as from 100 to 350 mesh, such as from 125 to 300 mesh and including from 150 mesh to 250 mesh. In certain embodiments, the fine mesh is 170 mesh.

Agitation of the shaking deck results in stamens and larger floral material being retained by the top coarse mesh screen while viable anthers are retained in the fine mesh screen at the second level. Dehisced anthers, dust and fine particles are retained in the bottom basin. The separated material at each level can be collected and stored until desired.

In embodiments, anthers containing viable pollen are collected and dried. Depending on the source of the anthers and target plants for the subject compositions, drying the anthers may vary. In some embodiments, the anthers are dried under ambient conditions (e.g., ambient pressure and temperature). In other embodiments, anthers are dried under reduced pressure. In other embodiments, anthers are dried under elevated pressure. In yet other embodiments, anthers are dried under elevated temperatures. In still other embodiments, anthers are dried under elevated temperatures and reduced pressures. The anthers may be dried by any convenient drying protocol, including but not limited to tumblers, shakers, rotary cylinders, under a stream of gas, and combinations thereof, among other drying protocols. The duration of drying may vary, depending on the source of anthers and desired water content in the pollen composition. In some embodiments, the anthers are dried for a duration which ranges from about 0.1 hours to about 100 hours, such as from about 0.5 hours to about 96 hours, such as from about 0.75 hours to about 72 hours, such as from 1 hour to 48 hours and including from about 2 hours to about 24 hours. In some instances, the anthers are dried for about 24 hours. In certain embodiments, the anthers are dried for a duration which is sufficient to obtain pollen having a desired water content, such as pollen having a water content of from 0.1% to 15% w/w, such as from 0.5% to 14% w/w, such as from 1% to 13% w/w, such as from 2% to 12% w/w, such as from 3% to 11% w/w and including from 5% to 10% w/w. In certain instances, the anthers are dried for a duration which is sufficient to obtain pollen having a water content from 8% to 10% w/w.

In some embodiments, the anthers are dried under dehumidified conditions, such as in a room or vessel with a relative humidity ranging from 0.01% to 25% relative humidity, such as from 0.05% to 20% relative humidity, such as from 0.1% to 15% relative humidity, such as from 0.5% to 10% relative humidity and including from 1% to 8% relative humidity.

In some embodiments, anthers are dried under a stream of gas. By "under a stream of gas" is meant that a flow of gas is contacted with anthers which results in at least some evaporation of water from the pollen-containing anthers. The flow of gas may be constant or in discrete intervals. Where the stream of gas is constant, the gas may contacted with the anthers at a rate of 0.01 L/min or more, such as at a rate of 0.05 L/min or more, such as at a rate of 0.1 L/min or more, such as at a rate of 0.5 L/min or more, such as at a rate of 0.75 L/min or more, such as at a rate of 1 L/min or more, such as at a rate of 2.5 L/min or more, such as at a rate of 5 L/min or more and including at a rate of 10 L/min or more. Where gas is applied in discrete intervals, the duration of each applied gas stream may vary and may be for 1 minute or more, such as for 5 minutes or more, such as for 10 minutes or more, such as for 30 minutes or more, such as for 60 minutes or more, such as for 120 minutes or more, such as for 240 minutes or more and including for 300 minutes or more. Likewise, the flow rate during each interval may vary where the stream of gas may be contacted with the anthers at a rate of 0.01 L/min or more, such as at a rate of 0.05 L/min or more, such as at a rate of 0.1 L/min or more, such as at a rate of 0.5 L/min or more, such as at a rate of 0.75 L/min or more, such as at a rate of 1 L/min or more, such as at a rate of 2.5 L/min or more, such as at a rate of 5 L/min or more and including at a rate of 10 L/min or more.

Pollen grains may, in certain embodiments, be dislodged from the anthers to obtain pure pollen grains. In these embodiments, the pollen is dislodged from the anthers such the pollen composition includes substantially only the grains of pollen and do not include anther sacs, filaments, chaff from flowers and other impurities. Accordingly, where the pollen component is pure pollen grains, the pollen is separated in a manner sufficient to produce a composition having 99% w/w or greater pollen grains, such as 99.5% w/w or greater pollen grains, such as 99.7% w/w or greater pollen grains, such as 99.9% w/w or greater pollen grains and including 99.99% w/w or greater pollen grains. In other words, pure pollen includes impurities in an amount of 1% w/w or less, such as 0.5% w/w or less, such as 0.3% w/w or less, such as 0.1% w/w or less and including impurities in an amount of 0.01% or less.

The pollen may be employed in the subject compositions and methods immediately or may be stored for a predetermined period of time. Where the pollen is stored, the pollen may be stored for a duration of 1 hour or longer, such as for 5 hours or longer, such as for 10 hours or longer, such as for 24 hours or longer, including for 2 days or longer, such as for 7 days or longer and including for 1 month or longer. The pollen may be stored under any conditions as desired. In some embodiments, the pollen is stored under ambient conditions, such as where the pollen will be stored for 24 hours or less. In other embodiments, the pollen is stored under reduced pressure, such as at a pressure of $10^{-1}$ torr or less, such as at a pressure of $10^{-2}$ torr or less, such as at a pressure of $10^{-3}$ torr or less, such as at a pressure of $10^{-4}$ torr or less, such as at a pressure of $10^{-5}$ torr or less, such as at a pressure of $10^{-6}$ torr or less and including at a pressure of $10^{-7}$ torr or less. In other embodiments, the pollen is stored at a reduced temperature, such as at a temperature of 10° C. or less, such as at a temperature of 5° C. or less, such as at a temperature of 0° C. or less, such as at a temperature of −10° C. or less, such as at a temperature of −25° C. or less, such as at a temperature of −50° C. or less, such as at a temperature of −75° C. or less and including at a temperature of −100° C. or less.

In some instances, the pollen is stored under dehumidified conditions, such as in a room or vessel with a relative humidity ranging from 0.0001% to 5% relative humidity, such as from 0.0005% to 4% relative humidity, such as from 0.001% to 3% relative humidity, such as from 0.005% to 2% relative humidity and including from 0.01% to 1% relative humidity.

Methods according to certain embodiment may also include determining and assessing the pollen grains. Assessing the pollen grains refers to the analysis of one or more of the properties and/or the components present in the pollen grains obtained from the subject plants. Determining the makeup of the pollen grains obtained from the subject plants may include, but is not limited to, determining the viability, the germanability or the fertility of the pollen grains, determining the organic composition, the metal composition, salt composition, ionic composition, organometallic composition, pH, physical properties (e.g., boiling point), electrochemical properties, spectroscopic properties, acid-base properties, polydispersities and isotopic composition of the pollen grains. Any convenient protocol can be employed to assess the pollen grains obtained from the subject plants. Methods for analyzing the pollen grains may include, but are not limited to staining the pollen grains (e.g., tetrazolium stain), in vitro culturing, in situ fertilization, the use of nuclear magnetic spectroscopy, UV-vis spectroscopy, infrared spectroscopy, high performance liquid chromatography, liquid chromatography-mass spectrometry, inductively coupled plasma emission spectrometry, inductively coupled plasma mass spectrometry, ion chromatography, X-ray diffraction, gas chromatography, gas chromatography-mass spectrometry, flow-injection analysis, scintillation counting, acidimetric titration, and flame emission spectrometry.

Determining and assessing pollen grains may be performed at any time during preparation as described above. For example, determining and assessing the pollen grains may be performed at predetermined intervals during storage such as every day, every week, every two weeks, every month, etc. Alternatively, determining and assessing the pollen grains may be performed in conjunction with methods for applying the subject compositions as described above. For example, the pollen grains may be sampled between intervals during a multiple application interval. The pollen grains may be evaluated 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions.

Figure 2:
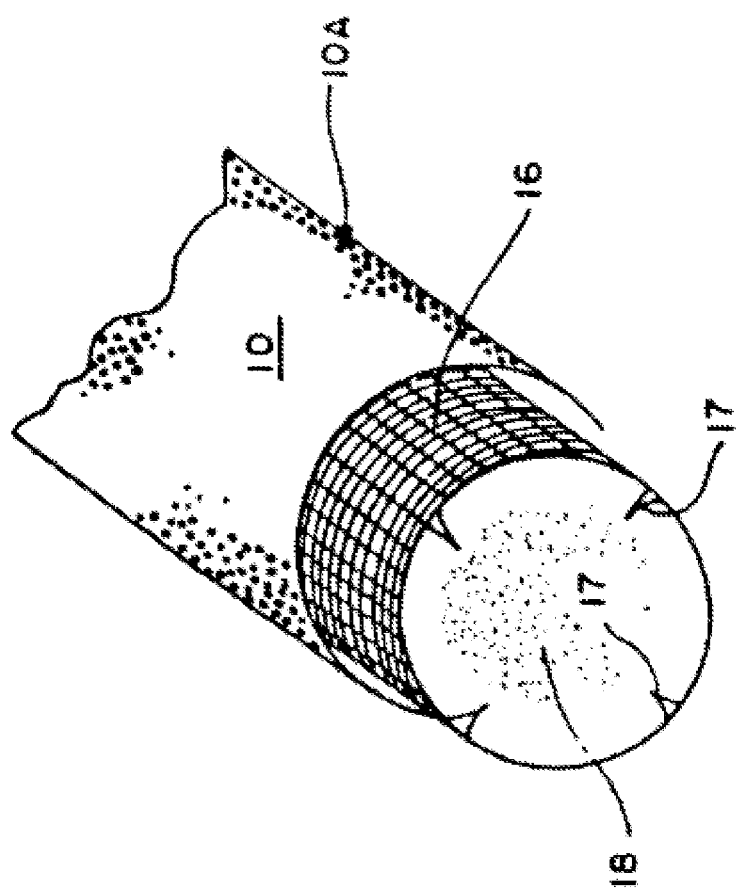
FIG. 2 is a fragmentary perspective view of a drying tube of an apparatus for processing pollen showing an interior sleeve according to certain embodiments.
Figure 3:
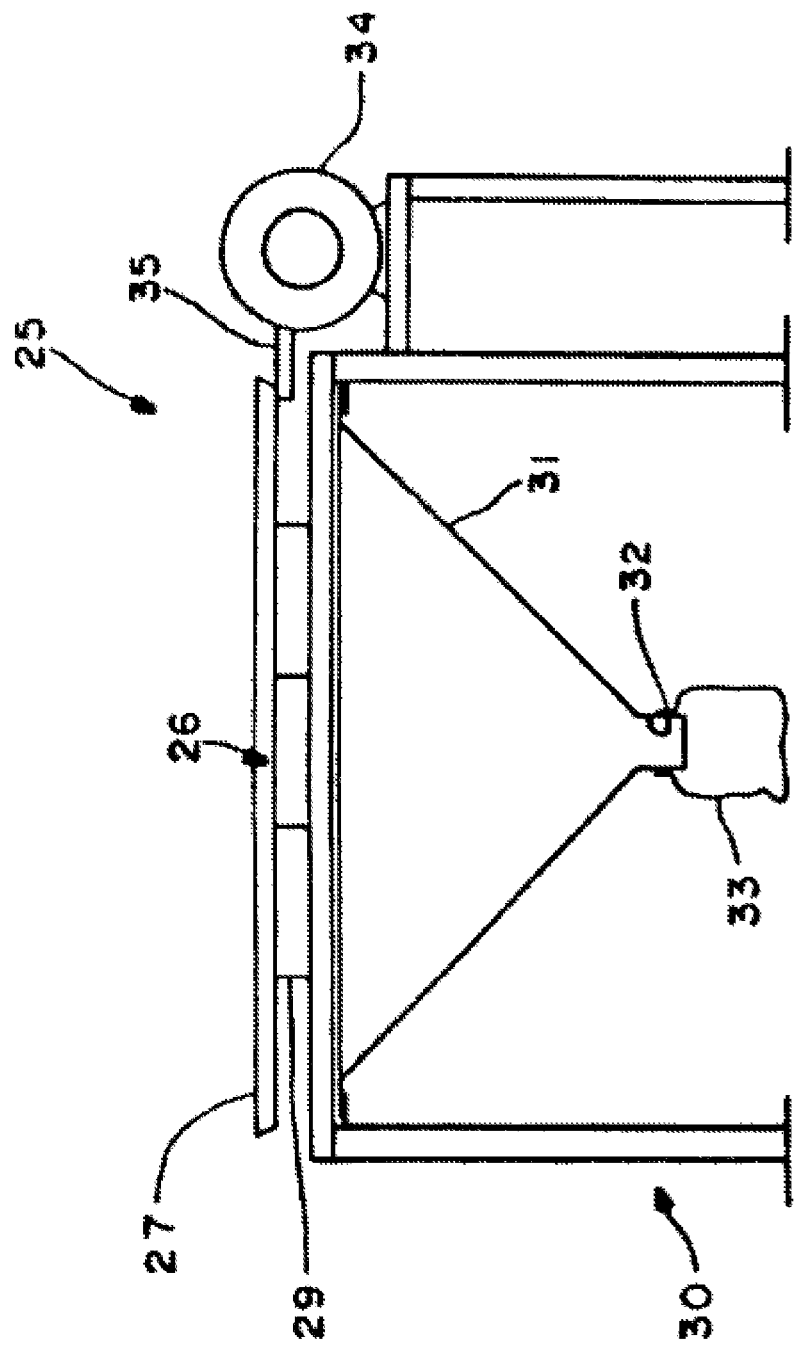
FIG. 3 is a diagrammatic view of a shake table used to separate pollen grains from anthers according to certain embodiments.
Figure 4:
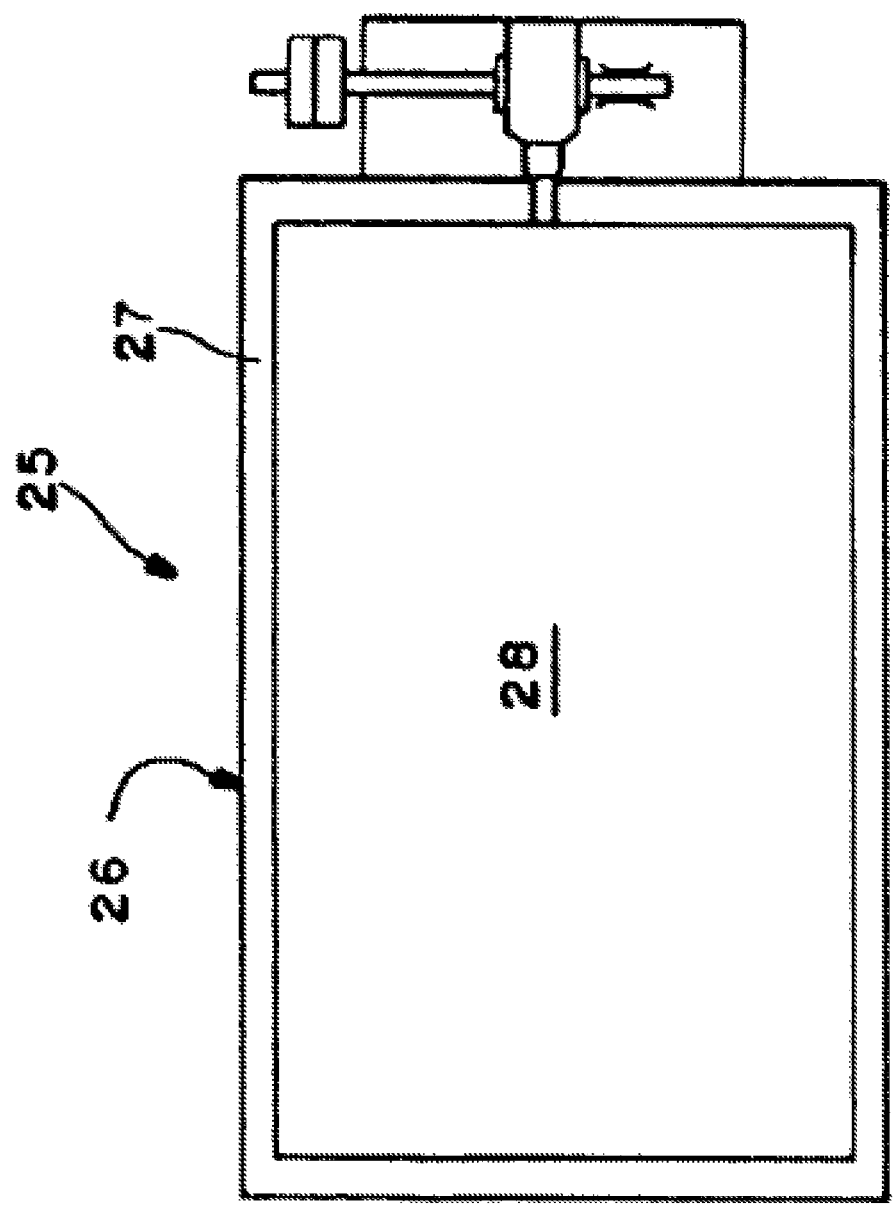
FIG. 4 is a top plan view of a shake table used to separate pollen grains from anthers according to certain embodiments.

In certain embodiments, apparatus suitable for processing pollen as described above may include those shown in FIGS. 1 to 4 in which:

FIG. 1 is a diagrammatic top view of drying apparatus; FIG. 2 is a fragmentary perspective view of one of the drying tubes of FIG. 1 broken away to reveal an interior sleeve; FIG. 3 is a diagrammatic view of a shake table used to separate pollen grains from anthers; and FIG. 4 is a top plan view of the shake table of FIG. 3.

Referring now to FIGS. 1 and 2 a number of perforated cylinders 10, for example five in number, are provided which are suitably supported in horizontal position parallel to one another and are rotated about their longitudinal axes by a motor 11, rubber disks 12 bearing against the tubes and suitable connecting means indicated generally as 13 so that the tubes are rotated at a suitable speed, for example 15 to 30 rpm. An electric fan and heater 14 blows heated air through a manifold 15 and into the ends of tubes 10. The air may be maintained in a dehumidified condition and at a suitable temperature, for example a moisture content of 20 to 40 relative humidity and a temperature of 18 to 25° C. For example, the apparatus may be operated in a dehumidified room and the air is preferably treated chemically, for example by contact with potassium permanganate to eliminate potentially harmful substances such as ethylene and aromatics which are produced by organic material such as the anthers which are being treated, such material being harmful to the pollen.

Referring now to FIG. 2, one of the cylinders 10 including its perforations 10A is shown and is broken away to reveal an inner sock or sleeve 16. The sock 16 is formed by stitching four segments of material together and is then turned inside out so that the unions 17 project inwardly to act as louvers to agitate and tumble the anthers which are shown at 18. The sock 16 is fixed to the interior surface of the cylinder 10 by any suitable means. The sock 16 may be made of 225 mesh nylon, although other materials may be used and the mesh size will vary according to the species of anthers. The duration of this drying may vary, such as for example, 24 hours. The dried anthers are then removed from the cylinders 10 and are placed on a shake table 25 which is shown in FIG. 3. The drying process may be carried out continuously or in a batchwise manner.

Referring now to FIGS. 3 and 4, the shake table 25 comprises a tray 26 having a rim 27 and a perforated bottom 28 supported by flexible members 29 on a frame 30. A funnel 31 is supported by the frame 30 beneath the tray 26 and at its lower end the funnel is fitted with a spout 32 over which a bag 33 may be slipped. A motor 34 is supported on the frame 30 and is connected by a reciprocating connector 35 to the tray 26. The bottom 28 of the tray is perforated, being conveniently formed by wire mesh screen having a mesh size such as to pass the liberated pollen grains but to hold back the remnants of the anthers left after crushing them to release the pollen grains. For example, the mesh size for anthers of almonds may be 170 mesh.

The motor 34 is operated to shake the tray at a suitable oscillatory speed, for example 400 to 500 cycles per minute. Meanwhile the anthers are gently rubbed by hand or by means of brushes, the pressure being sufficient to break open the anthers to liberate the pollen grains but insufficient to damage the pollen grains. The shaking action causes the pollen grains to fall through the screen 28 as they are released from the anthers, thereby limiting damage to the pollen grains due to the rubbing action.

Kits

Also provided are kits, where kits at least include one or more, e.g., a plurality of the subject pollination enhancing compositions, as described above. In certain embodiments, the subject pollination enhancing compositions in the kits may be provided in a package. For example, the pollination enhancing compositions of the kits may be presented in individual pouches, bottles, or analogous containers, to preserve the pollination enhancing compositions until use. For example, one form of suitable packaging is an air-tight container, air-tight bag, re-sealable water-tight/air-tight container, water-impermeable plastics material (e.g., polyvinylchloride), etc.

In certain embodiments, kits may include a separate amount of each component of the subject compositions (e.g., carbon skeleton compound, vitamin mix, micronutrients, pure pollen grains, etc.) where the user can mix each component separately in proportions desired, prior to application. In these embodiments, kits may further include one or more containers for mixing the subject compositions as well as a measuring device for portioning out each component, as desired.

As described above, pollination enhancing compositions are dry compositions. As such, the subject compositions contain little to no water. Accordingly, kits provided herein may further include a dessicant compound which absorbs atmospheric moisture during storage of the subject compositions. In embodiments, the dessicant may be any convenient hygroscopic compound which induces or sustains the moisture content of the subject compositions during storage such that the water content of the subject compositions remains 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. The dessicant may be contained in a separate package so that it does not contaminate the subject compositions, for example in a mesh bag, opened container, or air/water permeable polymeric or non-polymeric package. Dessicants of interest may include, but are not limited to silica gel, propylene glycol, hexylene glycol, butylene glycol, glycerol triacetate, vinyl alcohol, neoagarobiose, glycerol, sorbitol, xylitol, maltitol, polydextrose, quillaia, lactic acid, urea, glycerin, aloe vera gel, activated alumina, aerogel, benzophenone, bentonite clay, calcium chloride, calcium sulfate, colbalt(II) chloride, copper(II) sulfate, lithium chloride, lithium bromide, magnesium sulfate, magnesium perchlorate, molecular sieves, potassium carbonate, sodium, sodium chlorate, sodium chloride, sodium hydroxide, sodium sulfate, sucrose and phosphorus pentoxide, among other dessicants.

Kits may further include components for practicing the subject methods, such as devices for applying the pollination enhancing compositions (e.g., nozzle heads for sprayers or applicators), cartridges having a loaded predetermined amount of the subject compositions, measuring cups or devices for portioning desired amounts for application.

In addition, kits may also include instructions for how to use the subject pollination enhancing compositions, where the instructions may include information about to how to apply the compositions to foliage of subject flora (e.g., almond orchards), sources of biotic vectors (e.g., beehives), application interval schedules, and record keeping devices for executing an application interval regimen. The instructions are recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

The dry pollination enhancing compositions of the subject invention find use in applications where enhanced pollination is needed or desired. Applications for the subject composition include increasing the effective cross-pollination of subject flora, such as by: increasing the number of biotic vectors which visit a site in need of pollination (e.g., fruit orchards); increasing the amount of time a biotic vector will spend at the site in need of pollination; increasing the specificity of biotic vectors for a particular site in need of pollination; improving the overall nutritional health and activity of biotic vectors, increasing the overall production of crops from enhanced pollination; and the like.

The subject methods, i.e., foliar application of the aqueous composition, may result in an enhancement of growth of the plant that is treated, as compared to a control. By enhancement of growth is meant that over a set period of time, the treated plant attains a higher total mass than the control. The amount of enhancement will typically be at least about 5%, usually at least about 10% and more usually at least about 25%, where in many embodiments the amount of enhancement may be 50% or greater. In many embodiments, the amount of enhancement will be at least about 100%.

Embodiments of the invention result in enhancement of crop yield, e.g., by 5-fold or more, 10-fold or more, 15-fold or more, 20-fold or more, etc, where the amount of enhancement may be 25% or greater, e.g., 50% or greater.

A variety of different plants may be treated according to the subject methods, where such plants include both crop and ornamental plants, as described above.

All of the above figures are based on comparisons to a suitable control, e.g., flora or biotic vectors not treated with the subject compositions or with compositions which do not include one or more sources of extracted humate.

The following experiments are offered by way of illustration and not by way of limitation.

EXPERIMENTAL

I. Formulation of Pollination Enhancer

Example formulations for pollination enhancers according to certain embodiments are summarized in Tables 1 and 2.

TABLE 2

Example Pollination Enhancer

| Materials | Rate/ 2,000 lbs | Rate/ 5 lbs | Comments |
| --- | --- | --- | --- |
| Corn Starch | 660 lb | 1.65 lb | Blend all materials |
| Powdered Sugar | 1,100 lb | 2.75 lb | homogeneously. |
| Ca Gluconate | 320 lb | 0.8 lb | Use sealable containers that |
| Vitamin Mix | 20 lb | 0.05 lb | avoid moisture and air from |
| 4-GABA | 20 lb | 0.05 lb | getting into the product. |
| Folic Acid B12 | 20 lb | 0.05 lb | Keep stored under cool |
| Leonardite Fines | 20 lb | 0.05 lb | conditions (below 65° F.) |
| Fulvic Acid Fines | 20 lb | 0.05 lb | until used. Reseal partially |
| Boric Acid Fines | 30 gr | 75 mg | used containers. |

TABLE 2

Example Pollination Enhancer Formulation with Pollen

| Materials | Rate/ 2,500 lbs | Rate/ 6.25 lbs | Comments |
| --- | --- | --- | --- |
| Corn Starch | 350 lb | 1.65 lb | Blend all materials |
| Powdered Sugar | 1,110 lb | 2.75 lb | homogeneously. Use sealable |
| Ca Gluconate | 320 lb | 0.8 lb | containers that avoid moisture |
| Vitamin Mix | 20 lb | 0.05 lb | and air from getting into the |
| 4-GABA | 20 lb | 0.05 lb | product. |
| Folic Acid B12 | 20 lb | 0.05 lb | Keep stored under cool |
| Leonardite Fines | 20 lb | 0.05 lb | conditions (below 35° F.) |
| Fulvic Acid Fines | 20 lb | 0.05 lb | until used. Reseal partially |
| Boric Acid Fines | 30 gr | 75 mg | used containers. |
| Pollen | 500 lb | 1.25 lb | |

I. Field Tests for Honeybee Attractant and Pollination Enhancer

A. Nutritional Supplement and Attractant for Honeybees

The true test of a bee attractant/bee food is to get them excited despite the cool temperatures and to get them to fly in the early morning or late afternoon. A formulation according to Tables 1 and 2 above were produced. We placed a mound of the dry composition near the entrance to the hive. This was done in the early morning when temperatures were 40° F. and sunlight was scarce. Under normal conditions, bees will wait for the sunlight to be near 8,000 foot candles with temperatures above 60° F. before they resume activity. Within 5 seconds after placing the composition near the entrance, bees started to emerge. They immediately walked towards the mound and then started to roll in the product getting it all over their body. Many of the excited bees would then take flight. Further, and most importantly, over the course of one month it became evident that the composition we fed the bees was improving their health and rendered a large degree of resistance to pesticides, parasites and disease organisms. The numbers of cadavers outside the beehive was just a fraction of the toll outside the hives of untreated hives. In certain instances, honeybees contacted with the compositions of the invention preferentially work for specific orchards, such as for example orchards which contain similar compositions contacted with the foliage of the orchard.

B. Application of Compositions for Enhancing Pollination

We used a hand-held duster equipped with a squirrel cage blower and blew into the hive at the entrance slot. At the same time, we applied a pollination enhancer composition to the blocks using a backpack blower or via aircraft. The first day took some time for the bees to locate the blocks. However, once they detected the rich source of nectar and pollen in the treated blocks, the bee activity gained such a degree of activity that it became dangerous to get anywhere near the block.

In certain trials, the pollination enhancer composition included viable pollen grains collected from trees. The pollen grains used were processed down to pure pollen grains, which excluded anther sacs, filaments and chaff from the flowers. However, it was difficult to dislodge the pollen grains electrolitically held onto the anther sacs and debris. Through experiments conducted with pure pollen grains, we estimated that the purity of the pollen made it 12-16 times more effective than pollen products which include anther sacs, filaments, chaff from flowers and other impurities from traditional pollen harvesting.

Test I: Enhanced Attraction to Honeybees

The below study demonstrates that pollination enhancer compositions described herein increase attraction of biotic vectors. By applying the subject compositions, an increase of biotic vectors will visit the geographical area where the composition is applied as compared to suitable controls.

Method:

Apply the pollination enhancer composition according to either Table 1 or 2 to a platform at a set distance from the hive. Observe the number of honeybee visitations within a predetermined period of time. Table sugar, honey and flowers were employed as controls. Three hives were placed in the test area. The period of time allowed for visitation following placement of attractants was 3 hours. Start time was 5:30 am (March) at which time the temperature was 42° F. By 8:30 the temperature had risen to 53° F.

TABLE 3

| Results: | | | | |
|---|---|---|---|---|
| Composition | 20 feet | 50 feet | 100 feet | 100 yards |
| Table Sugar | 65 | 34 | 12 | 5 |
| Honey | 113 | 84 | 55 | 33 |
| Rose Flowers | 48 | 55 | 44 | 21 |
| Pollination Enhancer according to Table 1 above without pollen | 178 | 136 | 115 | 96 |

As demonstrated by the results shown in Table 3, the subject pollination enhancers showed greater ability to attract honeybees at all distances as compared to control compounds (i.e., table sugar, honey and rose flowers). From this study, it can be determined that pollination enhancer compositions of interest are sufficient to attract biotic vectors to subject flora applied compositions of the invention.

Test II: Enhanced Activity by Honeybees

The below study demonstrates that pollination enhancer compositions described herein increase the activity of biotic vectors. By applying the subject compositions to the source of biotic vector (i.e., honeybee hive), and increase in attraction and activity by the honeybee was observed.

Method:

Apply the product to the entrance of the hive during a period when the temperatures are below 50° F. and observe if the bees come out to retrieve the material and if they begin to activate their work. The period of exposure was 2 hours beginning at 6 am until 8 am. The temperature was 43° F. at 5:30 am in March.

TABLE 4

| Results: | | | | | | |
|---|---|---|---|---|---|---|
| Composition | Hive 1 | Hive 2 | Hive 3 | Hive 4 | Hive 5 | Mean |
| Table Sugar | 7 | 9 | 6 | 7 | 8 | 7 a |
| Honey | 20 | 26 | 33 | 35 | 28 | 28 b |
| Rose Flowers | 9 | 11 | 13 | 9 | 12 | 11 a |
| Pollination Enhancer according to Table 1 above without pollen | 67 | 85 | 93 | 97 | 88 | 86 c |

As demonstrated by the results shown in Table 4, the subject pollination enhancers showed greater ability to attract and increase the activity of honeybees as compared to control compounds (i.e., table sugar, honey and rose flowers). From this study, it can be determined that pollination enhancer compositions of interest are sufficient to attract and increase the activity of biotic vectors to subject flora applied compositions of the invention.

Test III: Nutritional Supplement for Honeybees

A test of the nutritional strength of the subject compositions to affect the positive health of the honeybees. Bees were fed for 30 consecutive days. After this feeding period, the hives were examined for the general activity around each hive and rated on a scale of 0-10 with 10 representing superior activity.

TABLE 5

| Results: | | | | | | |
|---|---|---|---|---|---|---|
| Composition | Hive 1 | Hive 2 | Hive 3 | Hive 4 | Hive 5 | Mean |
| Table Sugar | 3 | 3 | 2 | 3 | 3 | 3 a |
| Honey | 5 | 5 | 6 | 5 | 6 | 5 b |
| Rose Flowers | 2 | 2 | 2 | 1 | 1 | 2 a |
| Pollination Enhancer according to Table 1 above without pollen | 9 | 9 | 10 | 10 | 10 | 10 c |

Test V: Test for Priming of the Almond Orchards for Targeted Honeybee Activity

Beehives are first oriented with the entrance facing east. A hand-held duster with squirrel cage fan is then used to puff a composition prepared according to Table 1 above into the hive by puffing through the entrance opening. The bees' memory of their previous forage areas is erased. Bees have evolved to where they will direct their activities to the most lucrative of food sources in the field. At the same time that the hive is puffed, the almond blocks or field that need to be visited are dusted via an air applicator from the ground and/or an airplane. Once the bees are in tune with this rich source of nectar and pollen, they will direct their activities towards the, fields that have been coated with the identical composition of Table 1 above. The scale is set at 0-10.

TABLE 6

Results:

| Composition | 1 | 2 | 3 | 4 | 5 | Mean |
|---|---|---|---|---|---|---|
| Table Sugar | 2 | 2 | 2 | 2 | 2 | 2 a |
| Honey | 6 | 5 | 5 | 6 | 6 | 6 b |
| Rose Flowers | 1 | 2 | 1 | 1 | 1 | 1 a |
| Pollination Enhancer according to Table 1 above without pollen | 10 | 10 | 10 | 10 | 10 | 10 c |

TABLE 7

Effect on Yield and Quality of Almonds (in pounds):

| Composition | 1 | 2 | 3 | 4 | 5 | Mean |
|---|---|---|---|---|---|---|
| Table Sugar | 2300 | 2350 | 2100 | 2250 | 2370 | 2274 a |
| Honey | 3300 | 3250 | 3300 | 3500 | 3450 | 3360 b |
| Rose Flowers | 1900 | 2100 | 1980 | 1190 | 1920 | 1818 a |
| Pollination Enhancer according to Table 1 above without pollen | 4200 | 4500 | 4750 | 5200 | 5250 | 4780 c |

Average crackouts for the treatments were as follows:

Sugar=23%; Honey=24%; Rose Flower=22%; SureSet Apex=32%

As demonstrated by the results shown in Tables 6 and 7, the subject pollination enhancers showed greater ability to attract and increase the specificity of honeybees for orchards where the compositions had been applied as compared to control compounds (i.e., table sugar, honey and rose flowers). Furthermore, this increased attraction and activity showed a significant increase yield and quality of the crops produced (e.g., almonds).

Test VI: Reducing the Number of Blanks Per Tree with Compositions for Enhanced Pollination Blanks are almonds that develop the shell and hull but are absent in developing nut. These are commonly the result of incomplete pollination. By employing compositions described herein, the number of blanks can be significantly reduced by enhancing pollination.

TABLE 8

Number of Blanks per Tree

| Composition | 1 | 2 | 3 | 4 | 5 | Mean |
|---|---|---|---|---|---|---|
| Table Sugar | 125 | 158 | 168 | 204 | 198 | 171 c |
| Honey | 64 | 58 | 69 | 75 | 69 | 67 b |
| Rose Flowers | 178 | 189 | 178 | 188 | 199 | 186 c |
| Pollination Enhancer according to | 25 | 19 | 24 | 33 | 15 | 23 a |

TABLE 8-continued

Number of Blanks per Tree

| Composition | 1 | 2 | 3 | 4 | 5 | Mean |
|---|---|---|---|---|---|---|
| Table 1 above without pollen | | | | | | |

Mean not followed by a common letter are significantly different at the 5% level of confidence.
Note:
Blanks are almonds that develop the shell and the hull but are absent in the developing nut. They are commonly the result of incomplete pollination.

Beehives are first oriented with the entrance facing east. A hand-held duster with squirrel cage fan is then used to puff a composition prepared according to Table 1 above into the hive by puffing through the entrance opening. The bees' memory of their previous forage areas is erased. Bees have evolved to where they will direct their activities to the most lucrative of food sources in the field. At the same time that the hive is puffed, the almond blocks or field that need to be visited are dusted via an air applicator from the ground and/or an airplane. Once the bees are in tune with this rich source of nectar and pollen, they will direct their activities towards the, fields that have been coated with the identical composition of Table 1 above. The scale is set at 0-10.

Pollen Preparation

Closed blossoms are collected mechanically using a standard shaker-catch frame unit. Blossoms are immediately placed through a low rpm shredder, the cutting teeth of which are replaced by two parallel cylinders revolving inward to direct the flow of product. Cylinders are equipped with sheet metal screws (flat tipped with spiral groove on shaft) which extend from the inside of the cylinder wall to the periphery. The axis of the sheet metal screws pass directly through and are perpendicular to the central axis of the revolving cylinder. It is the gentle flailing by these teeth which dislodge mature anthers from the blossoms. A shaking deck and two levels of catch frames (one, a coarse five-mesh screen, the other a solid tin frame) provide a preliminary separation of anthers from expended blossoms. Anthers are further separated from extraneous materials through a shaking deck with three levels: (1) top, a ten-mesh stainless steel screen (sss); (2) middle, 20-mesh sss; and (3) bottom, a solid frame. Stamens and larger pieces are removed by the upper screen. Viable anthers fall through the first screen and are caught on the second level. Nonviable dehisced anthers, dust and finer extraneous materials are caught on the lower frame. The motion of the deck action carries product forward. The exit port of each level is staggered to deposit the three classes of materials into separate containers.

Pure anthers are then dried on racks lined with fine mesh, breathable nylon fabric. A second method for drying, developed by the author involves the use of slowly revolving perforated cylinders. Anthers are placed into a cylindrical 225-mesh nylon sock, which is cut to fit exactly into the inner diameter and length of the cylinder. A gentle stream of chemically filtered air is directed on the revolving cylinder, which along with the gentle tumbling action, facilitate drying. All drying is done in a dehumidified room with temperatures maintained between 18-25° C. An exhaust system, coupled with an air recirculating system keeps a constant, directed mass flow of air through the building. All recirculated air is purified with a permanganate filter which removes harmful concentrations of ethylene and aromatics. Drying is completed when pollen reaches 8-10% moisture. This occurs within 24 hours. The pollen and anthers are then placed on the separating table to further refine the product down to pure pollen grains. for most *Prunus* and *Pyrus* species, this is accomplished using a 200-mesh stainless steel screen supported by expanded metal. A gentle rubbing dislodges 95-100% of the pollen grains which fall to a catch frame. This pure pollen is either used immediately, placed under short-term storage (0° C.), or placed under long-term storage (−85° C.). Pollen is placed in double, vacuum, heat-sealed plastic bags before storage.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of enhancing pollination comprising:
   a) contacting a dry composition to foliage of one or more plants; and
   b) contacting the dry composition to a beehive,
   wherein the dry composition is in powdered form and comprises:
      a carbon skeleton energy compound in an amount of from 10% w/w to 60% w/w;
- macronutrients in an amount of from 1% w/w to 20% w/w;
- a vitamin cofactor composition in an amount of from 0.25% w/w to 3% w/w;
- micronutrients in an amount of from 0.01 ppm to 250 ppm;
- an ionophore;
- leonardite fines in an amount of from 0.05% w/w to 2% w/w; and
- fulvic acid powder in an amount of from 0.05% w/w to 2% w/w.

2. The method according to claim 1, wherein the dry composition is applied to the beehive simultaneously while applying to the foliage of the one or more plants.

3. The method according to claim 1, wherein the dry composition further comprises pollen obtained from the one or more plants.

4. The method according to claim 1, wherein the method comprises applying the dry composition to the one or more plants using an airplane crop duster and applying the dry composition to the beehive using a hand-held applicator.

5. The method according to claim 1, wherein the dry composition consists of:

- a carbon skeleton energy compound in an amount of from 10% w/w to 60% w/w;
- macronutrients in an amount of from 1% w/w to 20% w/w;
- a vitamin cofactor composition in an amount of from 0.25% w/w to 3% w/w;
- micronutrients in an amount of from 0.01 ppm to 250 ppm;
- an ionophore;
- leonardite fines in an amount of from 0.05% w/w to 2% w/w; and
- fulvic acid powder in an amount of from 0.05% w/w to 2% w/w.

6. The method according to claim 1, wherein the dry composition consists of:

- a carbon skeleton energy compound in an amount of from 10% w/w to 60% w/w;
- macronutrients in an amount of from 1% w/w to 20% w/w;
- a vitamin cofactor composition in an amount of from 0.25% w/w to 3% w/w;
- micronutrients in an amount of from 0.01 ppm to 250 ppm;
- an ionophore;
- pollen in an amount of from 2% w/w to 25% w/w;
- leonardite fines in an amount of from 0.05% w/w to 2% w/w; and
- fulvic acid powder in an amount of from 0.05% w/w to 2% w/w.

7. The method according to claim 1, wherein the leonardite fines comprises one or more elements selected from the group consisting of Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium(Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silica (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

8. The method according to claim 1, wherein the macronutrients are present in an amount ranging from 1% w/w to 15% w/w.

9. The method according to claim 1, wherein the dry composition further comprises a source of protein.

10. The method according to claim 1, wherein the dry composition is applied to the one or more plants twice during bloom.

11. The method according to claim 1, wherein the one or more plants are trees.

12. The method according to claim 1, wherein the method further comprises determining that the one or more plants are in need of enhanced pollination.

13. The method according to claim 1, wherein the micronutrients are present in an amount ranging from 0.01 ppm w/w to 200 ppm w/w.

14. The method according to claim 1, wherein the ionophore is an antibiotic or an amino butyric acid.

15. The method according to claim 14, wherein the ionophore is present in an amount ranging from 50 ppm to 500 ppm.

16. The method according to claim 1, wherein the carbon skeleton energy compound is a compound selected from the group consisting of powdered sugar, molasses, whey, corn steep liquor, grape syrup, maple syrup and corn syrup.

17. The method according to claim 16, wherein the carbon skeleton energy compound is powdered sugar.

18. The method according to claim 1, wherein the dry composition further comprises a flowing agent.

* * * * *